United States Patent
Bauman et al.

(10) Patent No.: US 8,591,876 B2
(45) Date of Patent: Nov. 26, 2013

(54) METHODS OF DECREASING SEBUM PRODUCTION IN THE SKIN

(75) Inventors: Susanne Bauman, Durham, NC (US); Nathan A. Stasko, Durham, NC (US)

(73) Assignee: Novan, Inc., Durham, NC (US)

( * ) Notice: Subject to any disclaimer, the term of this patent is extended or adjusted under 35 U.S.C. 154(b) by 0 days.

(21) Appl. No.: 13/325,826

(22) Filed: Dec. 14, 2011

(65) Prior Publication Data

US 2012/0156163 A1    Jun. 21, 2012

Related U.S. Application Data

(60) Provisional application No. 61/423,292, filed on Dec. 15, 2010, provisional application No. 61/504,634, filed on Jul. 5, 2011.

(51) Int. Cl.
*A61P 17/10*     (2006.01)
*C01B 21/24*     (2006.01)

(52) U.S. Cl.
USPC ............... 424/78.03; 424/78.07; 514/828; 514/859; 514/864; 514/887; 423/405

(58) Field of Classification Search
USPC ............... 424/78.03; 514/828, 859, 864, 887; 423/405
See application file for complete search history.

(56) References Cited

U.S. PATENT DOCUMENTS

| | | |
|---|---|---|
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,713,975 A | 12/1987 | Tomalia et al. |
| 4,737,550 A | 4/1988 | Tomalia |
| 4,857,599 A | 8/1989 | Tomalia et al. |
| 4,871,779 A | 10/1989 | Killat et al. |
| 4,985,023 A | 1/1991 | Blank et al. |
| 4,990,338 A | 2/1991 | Blank et al. |
| 5,035,892 A | 7/1991 | Blank et al. |
| 5,045,322 A | 9/1991 | Blank et al. |
| 5,061,487 A | 10/1991 | Blank et al. |
| 5,079,004 A | 1/1992 | Blank et al. |
| 5,380,758 A | 1/1995 | Stamler et al. |
| 5,405,919 A | 4/1995 | Keefer et al. |
| 5,418,301 A | 5/1995 | Hult et al. |
| 5,428,070 A | 6/1995 | Cooke et al. |
| 5,504,117 A | 4/1996 | Gorfine |
| 5,519,020 A | 5/1996 | Smith et al. |
| 5,525,357 A | 6/1996 | Keefer et al. |
| 5,574,068 A | 11/1996 | Stamler et al. |
| 5,593,876 A | 1/1997 | Stamler et al. |
| 5,599,984 A | 2/1997 | Bianchi et al. |
| 5,629,322 A | 5/1997 | Guthikonda et al. |
| 5,632,981 A | 5/1997 | Saavedra et al. |
| 5,650,442 A | 7/1997 | Mitchell et al. |
| 5,650,447 A | 7/1997 | Keefer et al. |
| 5,665,077 A | 9/1997 | Rosen et al. |
| 5,676,963 A | 10/1997 | Keefer et al. |
| 5,691,423 A | 11/1997 | Smith et al. |
| 5,693,676 A | 12/1997 | Gorfine |
| 5,700,830 A | 12/1997 | Korthuis et al. |
| 5,718,892 A | 2/1998 | Keefer et al. |
| 5,726,156 A | 3/1998 | Girten et al. |
| 5,750,573 A | 5/1998 | Bianchi et al. |
| 5,753,684 A | 5/1998 | Bianchi et al. |
| 5,760,001 A | 6/1998 | Girten et al. |
| 5,770,645 A | 6/1998 | Stamler et al. |
| 5,786,332 A | 7/1998 | Girten et al. |
| 5,789,447 A | 8/1998 | Wink, Jr. et al. |
| 5,797,887 A | 8/1998 | Rosen et al. |
| 5,810,010 A | 9/1998 | Anbar |
| 5,814,666 A | 9/1998 | Green et al. |
| 5,814,667 A | 9/1998 | Mitchell et al. |
| 5,821,261 A | 10/1998 | Durette et al. |
| 5,837,736 A | 11/1998 | Mitchell et al. |
| 5,840,759 A | 11/1998 | Mitchell et al. |
| 5,849,794 A | 12/1998 | Bianchi et al. |
| 5,852,058 A | 12/1998 | Cooke et al. |
| 5,854,289 A | 12/1998 | Bianchi et al. |
| 5,859,062 A | 1/1999 | Bianchi et al. |
| 5,861,168 A | 1/1999 | Cooke et al. |
| 5,863,890 A | 1/1999 | Stamler et al. |
| 5,891,459 A | 4/1999 | Cooke et al. |
| 5,891,472 A | 4/1999 | Russell |

(Continued)

FOREIGN PATENT DOCUMENTS

| | | |
|---|---|---|
| EP | 0 805 678 B1 | 10/2003 |
| EP | 0 746 327 B1 | 4/2004 |
| EP | 0 724 436 B1 | 7/2004 |
| EP | 1 411 908 B1 | 5/2005 |
| EP | 1 163 528 B1 | 11/2005 |
| EP | 1 681 068 A1 | 7/2006 |
| EP | 1 690 532 A1 | 8/2006 |
| EP | 1 690 554 A1 | 8/2006 |
| EP | 1 690 557 A1 | 8/2006 |

(Continued)

OTHER PUBLICATIONS

Amadeu et al. "Nitric Oxide Donor Improves Healing if Applied on Inflammatory and Proliferative Disease", *J. Surgical Reseach* 149:84-93 (2008).

(Continued)

*Primary Examiner* — Mina Haghighatian

(74) *Attorney, Agent, or Firm* — Myers Bigel Sibley & Sajovec, P.A.

(57) ABSTRACT

Provided herein are methods of using gaseous nitric oxide and/or at least one nitric oxide source to or decrease sebum production in the skin of a subject. In some embodiments, the nitric oxide source includes small molecule and/or macromolecular NO-releasing compounds.

7 Claims, No Drawings

(56) References Cited

U.S. PATENT DOCUMENTS

| | | |
|---|---|---|
| 5,910,316 A | 6/1999 | Keefer et al. |
| 5,932,538 A | 8/1999 | Garvey et al. |
| 5,958,427 A | 9/1999 | Salzman et al. |
| 5,961,466 A | 10/1999 | Anbar |
| 5,962,520 A | 10/1999 | Smith et al. |
| 5,994,294 A | 11/1999 | Garvey et al. |
| 5,994,444 A | 11/1999 | Trescony et al. |
| 5,999,843 A | 12/1999 | Anbar |
| 6,008,255 A | 12/1999 | Bianchi et al. |
| 6,022,900 A | 2/2000 | Bianchi et al. |
| 6,035,225 A | 3/2000 | Anbar |
| 6,043,358 A | 3/2000 | Caldwell et al. |
| 6,045,827 A | 4/2000 | Russell |
| 6,070,928 A | 6/2000 | Campbell |
| 6,087,479 A | 7/2000 | Stamler et al. |
| 6,103,275 A | 8/2000 | Seitz et al. |
| 6,110,453 A | 8/2000 | Keefer et al. |
| 6,143,037 A | 11/2000 | Goldstein et al. |
| 6,147,068 A | 11/2000 | Smith et al. |
| 6,151,522 A | 11/2000 | Alfano et al. |
| 6,160,021 A | 12/2000 | Lerner et al. |
| 6,171,232 B1 | 1/2001 | Papandreou et al. |
| 6,174,539 B1 | 1/2001 | Stamler et al. |
| 6,180,082 B1 | 1/2001 | Woltering et al. |
| 6,180,676 B1 | 1/2001 | Bianchi et al. |
| 6,190,704 B1 | 2/2001 | Murrell |
| 6,200,558 B1 | 3/2001 | Saavedra et al. |
| 6,207,855 B1 | 3/2001 | Toone et al. |
| 6,218,016 B1 | 4/2001 | Tedeschi et al. |
| 6,232,336 B1 | 5/2001 | Hrabie et al. |
| 6,232,434 B1 | 5/2001 | Stamler et al. |
| 6,238,683 B1 | 5/2001 | Burnett et al. |
| 6,248,787 B1 | 6/2001 | Bianchi et al. |
| 6,255,277 B1 | 7/2001 | Stamler et al. |
| 6,261,594 B1 | 7/2001 | Smith et al. |
| 6,270,779 B1 | 8/2001 | Fitzhugh et al. |
| 6,287,601 B1 | 9/2001 | Russell |
| 6,290,981 B1 | 9/2001 | Keefer et al. |
| 6,291,424 B1 | 9/2001 | Stamler et al. |
| 6,294,517 B1 | 9/2001 | Garvey et al. |
| 6,299,980 B1 | 10/2001 | Shah et al. |
| 6,323,211 B1 | 11/2001 | Garvey et al. |
| 6,350,467 B1 | 2/2002 | Demopoulos et al. |
| 6,352,709 B1 | 3/2002 | Stamler et al. |
| 6,358,536 B1 | 3/2002 | Thomas |
| 6,359,167 B2 | 3/2002 | Toone et al. |
| 6,359,182 B1 | 3/2002 | Stamler et al. |
| 6,369,071 B1 | 4/2002 | Haj-Yehia |
| 6,372,733 B1 | 4/2002 | Caldwell et al. |
| 6,377,321 B1 | 4/2002 | Khan et al. |
| 6,379,660 B1 | 4/2002 | Saavedra et al. |
| 6,379,691 B1 | 4/2002 | Tedeschi et al. |
| 6,391,895 B1 | 5/2002 | Towart et al. |
| 6,403,759 B2 | 6/2002 | Stamler et al. |
| 6,410,622 B1 | 6/2002 | Endres |
| 6,417,162 B1 | 7/2002 | Garvey et al. |
| 6,432,077 B1 | 8/2002 | Stenzler |
| 6,433,182 B1 | 8/2002 | Garvey et al. |
| 6,436,975 B1 | 8/2002 | Del Soldato |
| 6,441,254 B1 | 8/2002 | Dobert |
| 6,448,267 B1 | 9/2002 | Anggard et al. |
| 6,451,337 B1 | 9/2002 | Smith et al. |
| 6,455,542 B1 | 9/2002 | Anggard et al. |
| 6,469,065 B1 | 10/2002 | Garvey et al. |
| 6,471,978 B1 | 10/2002 | Stamler et al. |
| 6,472,390 B1 | 10/2002 | Stamler et al. |
| 6,474,508 B1 | 11/2002 | Marsh |
| 6,488,951 B2 | 12/2002 | Toone et al. |
| 6,492,405 B2 | 12/2002 | Haj-Yehia |
| 6,511,991 B2 | 1/2003 | Hrabie et al. |
| 6,514,934 B1 | 2/2003 | Garvey et al. |
| 6,538,033 B2 | 3/2003 | Bing |
| 6,560,478 B1 | 5/2003 | Alfano et al. |
| 6,562,344 B1 | 5/2003 | Stamler et al. |
| 6,562,785 B1 | 5/2003 | Shapiro |
| 6,583,113 B2 | 6/2003 | Stamler et al. |
| 6,583,311 B2 | 6/2003 | Toone et al. |
| 6,605,447 B2 | 8/2003 | Weiss et al. |
| 6,610,660 B1 | 8/2003 | Saavedra et al. |
| 6,627,602 B2 | 9/2003 | Stamler et al. |
| 6,642,208 B2 | 11/2003 | Cooke et al. |
| 6,642,260 B2 | 11/2003 | Haj-Yehia |
| 6,645,518 B2 | 11/2003 | Tedeschi et al. |
| 6,646,006 B2 | 11/2003 | Cooke et al. |
| 6,656,217 B1 | 12/2003 | Herzog, Jr. et al. |
| 6,673,891 B2 | 1/2004 | Stamler et al. |
| 6,699,846 B2 | 3/2004 | Elliott et al. |
| 6,703,046 B2 | 3/2004 | Fitzhugh et al. |
| 6,706,274 B2 | 3/2004 | Herrmann et al. |
| 6,709,681 B2 | 3/2004 | Benjamin et al. |
| 6,723,703 B2 | 4/2004 | Gaston et al. |
| 6,737,447 B1 | 5/2004 | Smith et al. |
| 6,747,062 B2 | 6/2004 | Murrell |
| 6,750,254 B2 | 6/2004 | Hrabie et al. |
| 6,758,214 B2 | 7/2004 | Fine et al. |
| 6,759,430 B2 | 7/2004 | Anggard et al. |
| 6,780,849 B2 | 8/2004 | Herrmann et al. |
| 6,793,644 B2 | 9/2004 | Stenzler |
| 6,796,966 B2 | 9/2004 | Thomas |
| 6,841,166 B1 | 1/2005 | Zhang et al. |
| 6,855,366 B2 | 2/2005 | Smith et al. |
| 6,875,840 B2 | 4/2005 | Stamler et al. |
| 6,887,485 B2 | 5/2005 | Fitzhugh et al. |
| 6,887,994 B2 | 5/2005 | Stamler et al. |
| 6,894,073 B2 | 5/2005 | Lee et al. |
| 6,896,899 B2 | 5/2005 | Demopolos et al. |
| 6,897,218 B2 | 5/2005 | Casella et al. |
| 6,911,433 B2 | 6/2005 | Saavedra et al. |
| 6,911,478 B2 | 6/2005 | Hrabie et al. |
| 6,946,484 B2 | 9/2005 | Adams et al. |
| 6,949,530 B2 | 9/2005 | Hrabie et al. |
| 6,951,902 B2 | 10/2005 | McDonald et al. |
| 6,964,984 B2 | 11/2005 | Stamler et al. |
| 6,974,801 B2 | 12/2005 | Honda et al. |
| 7,012,098 B2 | 3/2006 | Manning et al. |
| 7,015,347 B2 | 3/2006 | Toone et al. |
| 7,025,869 B2 | 4/2006 | Fine et al. |
| 7,030,238 B2 | 4/2006 | Stamler et al. |
| 7,033,999 B2 | 4/2006 | Stamler et al. |
| 7,040,313 B2 | 5/2006 | Fine et al. |
| 7,048,951 B1 | 5/2006 | Seitz et al. |
| 7,049,308 B2 | 5/2006 | Stamler et al. |
| 7,052,711 B2 | 5/2006 | West et al. |
| 7,070,798 B1 | 7/2006 | Michal et al. |
| 7,081,524 B2 | 7/2006 | Saavedra et al. |
| 7,087,588 B2 | 8/2006 | Del Soldato |
| 7,087,709 B2 | 8/2006 | Stamler et al. |
| 7,122,018 B2 | 10/2006 | Stenzler et al. |
| 7,122,027 B2 | 10/2006 | Trescony et al. |
| 7,122,529 B2 | 10/2006 | Ruane et al. |
| 7,128,904 B2 | 10/2006 | Batchelor et al. |
| 7,135,189 B2 | 11/2006 | Knapp |
| 7,135,498 B1 | 11/2006 | Chopp et al. |
| 7,157,500 B2 | 1/2007 | Stamler et al. |
| 7,169,809 B2 | 1/2007 | Berthelette et al. |
| 7,176,237 B2 | 2/2007 | Honda et al. |
| 7,179,475 B1 | 2/2007 | Burnett et al. |
| 7,189,761 B2 | 3/2007 | Gorfine |
| 7,199,154 B2 | 4/2007 | Berthelette et al. |
| 7,204,980 B2 | 4/2007 | Clark |
| 7,226,586 B2 | 6/2007 | Fitzhugh et al. |
| 7,234,079 B2 | 6/2007 | Cheng et al. |
| 7,259,250 B2 | 8/2007 | Stamler et al. |
| 7,279,176 B1 | 10/2007 | West et al. |
| 7,282,519 B2 | 10/2007 | Garvey et al. |
| 7,314,857 B2 | 1/2008 | Madhyastha |
| 7,335,383 B2 | 2/2008 | Meyerhoff et al. |
| 7,345,053 B2 | 3/2008 | Garvey |
| 7,348,319 B2 | 3/2008 | Hrabie et al. |
| 7,364,585 B2 | 4/2008 | Weber |
| 7,396,829 B2 | 7/2008 | Garvey et al. |
| 7,417,109 B2 | 8/2008 | Stamler et al. |
| 7,425,218 B2 | 9/2008 | Keefer et al. |
| 7,432,301 B2 | 10/2008 | Gaston et al. |

(56) References Cited

U.S. PATENT DOCUMENTS

| | | |
|---|---|---|
| 7,452,916 B2 | 11/2008 | Cooke |
| 7,468,435 B2 | 12/2008 | Waterhouse et al. |
| 7,485,324 B2 | 2/2009 | Miller et al. |
| 7,520,866 B2 | 4/2009 | Stenzler et al. |
| 7,531,164 B2 | 5/2009 | Daaka et al. |
| 7,569,559 B2 | 8/2009 | Arnold et al. |
| 7,582,623 B2 | 9/2009 | Mascharak |
| 7,595,313 B2 | 9/2009 | Garvey et al. |
| 7,622,501 B2 | 11/2009 | Dufresne et al. |
| 7,622,502 B2 | 11/2009 | Berthelette et al. |
| 7,645,748 B2 | 1/2010 | Orchansky et al. |
| 7,645,749 B2 | 1/2010 | Orchansky et al. |
| 7,651,697 B2 | 1/2010 | West et al. |
| 7,655,423 B2 | 2/2010 | Chopp et al. |
| 7,678,391 B2 | 3/2010 | Graham et al. |
| 7,678,830 B2 | 3/2010 | Honda et al. |
| 7,696,247 B2 | 4/2010 | Herrmann et al. |
| 7,745,656 B2 | 6/2010 | Toone et al. |
| 7,763,283 B2 | 7/2010 | Batchelor et al. |
| 7,785,616 B2 | 8/2010 | Stamler et al. |
| 7,795,286 B2 | 9/2010 | Lucet-Levannier |
| 7,799,335 B2 | 9/2010 | Herrmann et al. |
| 7,807,716 B2 | 10/2010 | Farber |
| 7,811,600 B2 | 10/2010 | Cheng et al. |
| 7,820,284 B2 | 10/2010 | Terry |
| 7,829,553 B2 | 11/2010 | Arnold et al. |
| 7,838,023 B2 | 11/2010 | Garvey et al. |
| 7,846,400 B2 | 12/2010 | Hyde et al. |
| 7,862,598 B2 | 1/2011 | Hyde et al. |
| 7,892,198 B2 | 2/2011 | Stenzler |
| 7,897,399 B2 | 3/2011 | Hyde et al. |
| 7,928,079 B2 | 4/2011 | Hrabie et al. |
| 7,928,096 B2 | 4/2011 | Waterhouse et al. |
| 7,947,299 B2 | 5/2011 | Knapp |
| 7,975,699 B2 | 7/2011 | Hyde et al. |
| 8,003,811 B2 | 8/2011 | Almirante |
| 8,017,074 B2 | 9/2011 | Arnold |
| 8,021,679 B2 | 9/2011 | Chen |
| 8,034,384 B2 | 10/2011 | Meyerhoff |
| 8,043,246 B2 | 10/2011 | Av-Gay et al. |
| 2001/0012851 A1 | 8/2001 | Lundy et al. |
| 2001/0025057 A1 | 9/2001 | Gorfine |
| 2001/0038832 A1 | 11/2001 | Bonavida et al. |
| 2001/0053772 A1 | 12/2001 | Bonavida et al. |
| 2002/0018757 A1 | 2/2002 | Harichian et al. |
| 2002/0028851 A1 | 3/2002 | Bianchi et al. |
| 2002/0049157 A1 | 4/2002 | Wu et al. |
| 2002/0061879 A1 | 5/2002 | Garvey et al. |
| 2002/0068365 A1 | 6/2002 | Kuhrts |
| 2002/0090401 A1 | 7/2002 | Tucker et al. |
| 2002/0132234 A1 | 9/2002 | Moskowitz |
| 2002/0136763 A1 | 9/2002 | Demopoulos et al. |
| 2002/0138051 A1 | 9/2002 | Hole et al. |
| 2002/0143007 A1 | 10/2002 | Garvey et al. |
| 2002/0143062 A1 | 10/2002 | Lopez-Berestein et al. |
| 2002/0155174 A1 | 10/2002 | Benjamin et al. |
| 2002/0161042 A1 | 10/2002 | Gorfine |
| 2002/0165195 A1 | 11/2002 | Wang et al. |
| 2002/0182162 A1 | 12/2002 | Shahinpoor et al. |
| 2003/0027844 A1 | 2/2003 | Soldato |
| 2003/0039697 A1 | 2/2003 | Zhao et al. |
| 2003/0050305 A1 | 3/2003 | Tejada |
| 2003/0072783 A1 | 4/2003 | Stamler et al. |
| 2003/0093143 A1 | 5/2003 | Zhao et al. |
| 2003/0134779 A1 | 7/2003 | Diarra et al. |
| 2003/0170674 A1 | 9/2003 | Moskowitz |
| 2003/0203915 A1 | 10/2003 | Fang et al. |
| 2003/0219854 A1 | 11/2003 | Guarna et al. |
| 2004/0009238 A1 | 1/2004 | Miller et al. |
| 2004/0013747 A1 | 1/2004 | Tucker et al. |
| 2004/0033480 A1 | 2/2004 | Wong |
| 2004/0037836 A1 | 2/2004 | Stamler et al. |
| 2004/0037897 A1 | 2/2004 | Benjamin et al. |
| 2004/0043068 A1 | 3/2004 | Tedeschi et al. |
| 2004/0076582 A1 | 4/2004 | Dimatteo et al. |
| 2004/0082659 A1 | 4/2004 | Cooke et al. |
| 2004/0105898 A1 | 6/2004 | Benjamin et al. |
| 2004/0110691 A1 | 6/2004 | Stamler |
| 2004/0131703 A1 | 7/2004 | Bach et al. |
| 2004/0143010 A1 | 7/2004 | Esteve-Soler et al. |
| 2004/0147598 A1 | 7/2004 | Haj-Yehia |
| 2004/0157936 A1 | 8/2004 | Burnett et al. |
| 2004/0228889 A1 | 11/2004 | Cals-Grierson |
| 2004/0254419 A1 | 12/2004 | Wang et al. |
| 2004/0265244 A1 | 12/2004 | Rosen |
| 2005/0036949 A1 | 2/2005 | Tucker et al. |
| 2005/0037093 A1 | 2/2005 | Benjamin |
| 2005/0054714 A1 | 3/2005 | Munoz et al. |
| 2005/0065161 A1 | 3/2005 | Garvey et al. |
| 2005/0069595 A1 | 3/2005 | Chen et al. |
| 2005/0074506 A1 | 4/2005 | Natan et al. |
| 2005/0079132 A1 | 4/2005 | Wang et al. |
| 2005/0080021 A1 | 4/2005 | Tucker et al. |
| 2005/0080024 A1 | 4/2005 | Tucker et al. |
| 2005/0131064 A1 | 6/2005 | Gaston et al. |
| 2005/0142217 A1 | 6/2005 | Adams et al. |
| 2005/0142218 A1 | 6/2005 | Tucker et al. |
| 2005/0152891 A1 | 7/2005 | Toone et al. |
| 2005/0165452 A1 | 7/2005 | Sigg et al. |
| 2005/0171006 A1 | 8/2005 | Bunting et al. |
| 2005/0171199 A1 | 8/2005 | Murrell |
| 2005/0187222 A1 | 8/2005 | Garvey et al. |
| 2005/0220838 A1 | 10/2005 | Zhao et al. |
| 2005/0245492 A1 | 11/2005 | Lephart et al. |
| 2005/0265958 A1 | 12/2005 | West et al. |
| 2005/0281867 A1 | 12/2005 | Kahn et al. |
| 2006/0008529 A1 | 1/2006 | Meyerhoff et al. |
| 2006/0009431 A1 | 1/2006 | Earl et al. |
| 2006/0035854 A1 | 2/2006 | Goldstein et al. |
| 2006/0039950 A1 | 2/2006 | Zhou et al. |
| 2006/0058363 A1 | 3/2006 | Wang et al. |
| 2006/0067909 A1 | 3/2006 | West et al. |
| 2006/0100159 A1 | 5/2006 | Stamler et al. |
| 2006/0142183 A1 | 6/2006 | Diarra et al. |
| 2006/0147553 A1 | 7/2006 | Miller et al. |
| 2006/0147904 A1 | 7/2006 | Wong |
| 2006/0172018 A1 | 8/2006 | Fine et al. |
| 2006/0198831 A1 | 9/2006 | Stamler et al. |
| 2006/0211601 A1 | 9/2006 | Stamler et al. |
| 2006/0269620 A1 | 11/2006 | Morris et al. |
| 2006/0286158 A1 | 12/2006 | Murrell et al. |
| 2006/0286159 A1 | 12/2006 | Murrell et al. |
| 2007/0003538 A1 | 1/2007 | Madhyastha |
| 2007/0014686 A1 | 1/2007 | Arnold et al. |
| 2007/0014733 A1 | 1/2007 | O'Donnell et al. |
| 2007/0014828 A1 | 1/2007 | Fitzhugh et al. |
| 2007/0037821 A1 | 2/2007 | Garvey et al. |
| 2007/0048344 A1 | 3/2007 | Yahiaoui et al. |
| 2007/0053952 A1 | 3/2007 | Chen et al. |
| 2007/0053955 A1 | 3/2007 | Larson et al. |
| 2007/0053966 A1 | 3/2007 | Ang et al. |
| 2007/0059351 A1 | 3/2007 | Murrell et al. |
| 2007/0086954 A1 | 4/2007 | Miller |
| 2007/0087025 A1 | 4/2007 | Fitzhugh et al. |
| 2007/0088345 A1 | 4/2007 | Larson et al. |
| 2007/0089739 A1 | 4/2007 | Fine et al. |
| 2007/0116785 A1 | 5/2007 | Miller |
| 2007/0148136 A1 | 6/2007 | Whitlock |
| 2007/0154570 A1 | 7/2007 | Miller et al. |
| 2007/0166227 A1 | 7/2007 | Liu et al. |
| 2007/0172469 A1 | 7/2007 | Clark |
| 2007/0191377 A1 | 8/2007 | Worcel |
| 2007/0196327 A1 | 8/2007 | Kalivretenos et al. |
| 2007/0197543 A1 | 8/2007 | Esteve-Soler et al. |
| 2007/0202155 A1 | 8/2007 | Ang et al. |
| 2007/0203242 A1 | 8/2007 | Calton |
| 2007/0207179 A1 | 9/2007 | Andersen et al. |
| 2007/0219208 A1 | 9/2007 | Kalyanaraman et al. |
| 2007/0225250 A1 | 9/2007 | Brown |
| 2007/0239107 A1 | 10/2007 | Lundberg et al. |
| 2007/0243262 A1 | 10/2007 | Hurley et al. |
| 2007/0248676 A1 | 10/2007 | Stamler et al. |
| 2007/0264225 A1 | 11/2007 | Cheng et al. |
| 2007/0270348 A1 | 11/2007 | Kahn et al. |

(56) References Cited

U.S. PATENT DOCUMENTS

| | | |
|---|---|---|
| 2007/0275100 A1 | 11/2007 | Miller |
| 2008/0025972 A1 | 1/2008 | Daaka et al. |
| 2008/0039521 A1 | 2/2008 | Yasuda et al. |
| 2008/0045909 A1 | 2/2008 | Fossel |
| 2008/0069848 A1 | 3/2008 | Peters |
| 2008/0069863 A1 | 3/2008 | Peters |
| 2008/0069905 A1 | 3/2008 | Peters |
| 2008/0071206 A1 | 3/2008 | Peters |
| 2008/0076721 A1 | 3/2008 | Abraham et al. |
| 2008/0089956 A1 | 4/2008 | Da et al. |
| 2008/0139450 A1 | 6/2008 | Madhyastha et al. |
| 2008/0145449 A1 | 6/2008 | Stamler |
| 2008/0171021 A1 | 7/2008 | Bach et al. |
| 2008/0171351 A1 | 7/2008 | Smith |
| 2008/0175881 A1 | 7/2008 | Ippoliti et al. |
| 2008/0182797 A1 | 7/2008 | Nudler et al. |
| 2008/0193385 A1 | 8/2008 | Maibach |
| 2008/0193566 A1 | 8/2008 | Miller et al. |
| 2008/0207491 A1 | 8/2008 | Diarra et al. |
| 2008/0207713 A1 | 8/2008 | Wang et al. |
| 2008/0214646 A1 | 9/2008 | Knaus et al. |
| 2008/0226751 A1 | 9/2008 | Tucker et al. |
| 2008/0241208 A1 | 10/2008 | Shanley et al. |
| 2008/0275093 A1 | 11/2008 | Garvey et al. |
| 2008/0280984 A1 | 11/2008 | Fossel |
| 2008/0286321 A1 | 11/2008 | Reneker et al. |
| 2008/0287861 A1 | 11/2008 | Stenzler et al. |
| 2008/0306012 A1 | 12/2008 | Hrabie et al. |
| 2008/0311163 A1 | 12/2008 | Peters |
| 2008/0317626 A1 | 12/2008 | Arnold et al. |
| 2008/0317679 A1 | 12/2008 | Tamarkin et al. |
| 2009/0004298 A1 | 1/2009 | Gaston et al. |
| 2009/0010989 A1 | 1/2009 | Peters |
| 2009/0018091 A1 | 1/2009 | Ellis et al. |
| 2009/0028966 A1 | 1/2009 | Chen et al. |
| 2009/0029028 A1 | 1/2009 | Garcin et al. |
| 2009/0036491 A1 | 2/2009 | Tucker et al. |
| 2009/0042819 A1 | 2/2009 | Ellis et al. |
| 2009/0048219 A1 | 2/2009 | Garvey |
| 2009/0069449 A1 | 3/2009 | Smith et al. |
| 2009/0081279 A1 | 3/2009 | Jezek et al. |
| 2009/0088411 A1 | 4/2009 | Renzi et al. |
| 2009/0093510 A1 | 4/2009 | Clementi et al. |
| 2009/0098187 A1 | 4/2009 | Peters et al. |
| 2009/0108777 A1 | 4/2009 | Hyde et al. |
| 2009/0110612 A1 | 4/2009 | Hyde et al. |
| 2009/0110712 A1 | 4/2009 | Hyde et al. |
| 2009/0110933 A1 | 4/2009 | Hyde et al. |
| 2009/0110958 A1 | 4/2009 | Hyde et al. |
| 2009/0112055 A1 | 4/2009 | Hyde et al. |
| 2009/0112193 A1 | 4/2009 | Hyde et al. |
| 2009/0112197 A1 | 4/2009 | Hyde et al. |
| 2009/0118819 A1 | 5/2009 | Merz et al. |
| 2009/0123528 A1 | 5/2009 | Fossel |
| 2009/0131342 A1 | 5/2009 | Ellis |
| 2009/0136410 A1 | 5/2009 | Smith |
| 2009/0137683 A1 | 5/2009 | Yasuda et al. |
| 2009/0143417 A1 | 6/2009 | Smith et al. |
| 2009/0148482 A1 | 6/2009 | Peters |
| 2009/0186859 A1 | 7/2009 | Velázquez et al. |
| 2009/0191284 A1 | 7/2009 | Conoci et al. |
| 2009/0196930 A1 | 8/2009 | Surber et al. |
| 2009/0197964 A1 | 8/2009 | Summar et al. |
| 2009/0203653 A1 | 8/2009 | Garvey |
| 2009/0214618 A1 | 8/2009 | Schoenfisch et al. |
| 2009/0214624 A1 | 8/2009 | Smith et al. |
| 2009/0214674 A1 | 8/2009 | Barraud et al. |
| 2009/0215838 A1 | 8/2009 | Garvey et al. |
| 2009/0221536 A1 | 9/2009 | Fossel |
| 2009/0222088 A1 | 9/2009 | Chen et al. |
| 2009/0226504 A1 | 9/2009 | Peters |
| 2009/0232863 A1 | 9/2009 | Cheng et al. |
| 2009/0232868 A1 | 9/2009 | Chen et al. |
| 2009/0255536 A1 | 10/2009 | Av-Gay et al. |
| 2009/0263416 A1 | 10/2009 | Dawson et al. |
| 2009/0264398 A1 | 10/2009 | Bauer |
| 2009/0270509 A1 | 10/2009 | Arnold et al. |
| 2009/0287072 A1 | 11/2009 | Meyerhoff et al. |
| 2009/0297634 A1 | 12/2009 | Friedman et al. |
| 2009/0304815 A1 | 12/2009 | Cossu et al. |
| 2009/0317885 A1 | 12/2009 | Mascharak |
| 2010/0003338 A1 | 1/2010 | Hubbell et al. |
| 2010/0015253 A1 | 1/2010 | Benjamin |
| 2010/0016790 A1 | 1/2010 | Peters |
| 2010/0021506 A1 | 1/2010 | Jones |
| 2010/0040703 A1 | 2/2010 | Miller et al. |
| 2010/0062055 A1 | 3/2010 | Herrmann et al. |
| 2010/0076162 A1 | 3/2010 | Ameer et al. |
| 2010/0086530 A1 | 4/2010 | Martinov |
| 2010/0087370 A1 | 4/2010 | Jain et al. |
| 2010/0098733 A1 | 4/2010 | Stasko |
| 2010/0099729 A1 | 4/2010 | Almirante et al. |
| 2010/0112033 A1 | 5/2010 | Ganzarolli de Oliveira et al. |
| 2010/0112095 A1 | 5/2010 | Morris et al. |
| 2010/0129474 A1 | 5/2010 | Benjamin et al. |
| 2010/0152683 A1 | 6/2010 | Lindgren et al. |
| 2010/0159119 A1 | 6/2010 | Chen et al. |
| 2010/0166603 A1 | 7/2010 | Opie |
| 2010/0178319 A1 | 7/2010 | Lindgren et al. |
| 2010/0184992 A1 | 7/2010 | Toone et al. |
| 2010/0196517 A1 | 8/2010 | Fossel |
| 2010/0197702 A1 | 8/2010 | Hellberg et al. |
| 2010/0197802 A1 | 8/2010 | Jezek et al. |
| 2010/0209469 A1 | 8/2010 | Bezwada |
| 2010/0221308 A1 | 9/2010 | Madhyastha et al. |
| 2010/0233304 A1 | 9/2010 | Pan |
| 2010/0239512 A1 | 9/2010 | Morris et al. |
| 2010/0247611 A1 | 9/2010 | Balkus, Jr. et al. |
| 2010/0247680 A1 | 9/2010 | Szabo |
| 2010/0255062 A1 | 10/2010 | Kalivretenos et al. |
| 2010/0256755 A1 | 10/2010 | Chen et al. |
| 2010/0261930 A1 | 10/2010 | Honda et al. |
| 2010/0262238 A1 | 10/2010 | Chen et al. |
| 2010/0268149 A1 | 10/2010 | Av-Gay et al. |
| 2010/0276284 A1 | 11/2010 | Meyerhoff et al. |
| 2010/0280122 A1 | 11/2010 | Fossel |
| 2010/0285100 A1 | 11/2010 | Balkus, Jr. et al. |
| 2010/0286272 A1 | 11/2010 | Perricone et al. |
| 2010/0297200 A1 | 11/2010 | Schoenfisch et al. |
| 2010/0303891 A1 | 12/2010 | Lee et al. |
| 2010/0311780 A1 | 12/2010 | Farber |
| 2010/0323036 A1 | 12/2010 | Fine |
| 2010/0324107 A1 | 12/2010 | Dos Santos et al. |
| 2010/0331542 A1 | 12/2010 | Smith |
| 2010/0331968 A1 | 12/2010 | Morris et al. |
| 2011/0008815 A1 | 1/2011 | Stamler et al. |
| 2011/0033437 A1 | 2/2011 | Smith et al. |
| 2011/0038965 A1 | 2/2011 | McKay et al. |
| 2011/0046182 A1 | 2/2011 | Gilmer et al. |
| 2011/0059036 A1 | 3/2011 | Arnold et al. |
| 2011/0059189 A1 | 3/2011 | Cisneros |
| 2011/0065783 A1 | 3/2011 | O'Donnell et al. |
| 2011/0070318 A1 | 3/2011 | Jezek et al. |
| 2011/0071168 A1 | 3/2011 | Chopp et al. |
| 2011/0076313 A1 | 3/2011 | Av-Gay et al. |
| 2011/0086234 A1 | 4/2011 | Stasko et al. |
| 2011/0104240 A1 | 5/2011 | Jones et al. |
| 2011/0106000 A1 | 5/2011 | Jones et al. |
| 2011/0195959 A1 | 8/2011 | Glick et al. |
| 2012/0021055 A1 | 1/2012 | Schoenfisch et al. |
| 2012/0134951 A1* | 5/2012 | Stasko et al. ............... 424/78.06 |

FOREIGN PATENT DOCUMENTS

| | | |
|---|---|---|
| EP | 1 690 558 A1 | 8/2006 |
| EP | 1 700 611 A1 | 9/2006 |
| EP | 1 704 876 A1 | 9/2006 |
| EP | 1 704 877 A1 | 9/2006 |
| EP | 1 704 879 A1 | 9/2006 |
| EP | 1 707 224 A1 | 10/2006 |
| EP | 1 728 438 A1 | 12/2006 |
| EP | 1 731 176 A1 | 12/2006 |
| EP | 1 757 278 A1 | 2/2007 |
| EP | 1 764 119 A1 | 3/2007 |

(56) References Cited

FOREIGN PATENT DOCUMENTS

| | | |
|---|---|---|
| EP | 1 790 335 A1 | 5/2007 |
| EP | 1 861 130 B1 | 9/2008 |
| EP | 1 343 547 B1 | 4/2009 |
| EP | 1 871 433 B1 | 4/2009 |
| EP | 1 161 248 B1 | 5/2009 |
| EP | 1 846 058 B1 | 7/2009 |
| WO | WO 95/07691 A1 | 3/1995 |
| WO | WO 95/10267 A1 | 4/1995 |
| WO | WO 95/12394 A1 | 5/1995 |
| WO | WO 95/19767 A1 | 7/1995 |
| WO | WO 95/22335 A1 | 8/1995 |
| WO | WO 95/32715 A1 | 12/1995 |
| WO | WO 96/08966 A1 | 3/1996 |
| WO | WO 96/13164 A1 | 5/1996 |
| WO | WO 96/14844 A1 | 5/1996 |
| WO | WO 96/15781 A1 | 5/1996 |
| WO | WO 96/15797 A1 | 5/1996 |
| WO | WO 96/27386 A1 | 9/1996 |
| WO | WO 96/32118 A1 | 10/1996 |
| WO | WO 96/32136 A1 | 10/1996 |
| WO | WO 96/33757 A1 | 10/1996 |
| WO | WO 96/35416 A1 | 11/1996 |
| WO | WO 97/16983 A1 | 5/1997 |
| WO | WO 97/31654 A1 | 9/1997 |
| WO | WO 97/34014 A1 | 9/1997 |
| WO | WO 97/47254 A1 | 12/1997 |
| WO | WO 98/05689 A1 | 2/1998 |
| WO | WO 98/06389 A1 | 2/1998 |
| WO | WO 98/08482 A2 | 3/1998 |
| WO | WO 98/08482 A3 | 3/1998 |
| WO | WO 98/08496 A1 | 3/1998 |
| WO | WO 98/13358 A1 | 4/1998 |
| WO | WO 98/19996 A1 | 5/1998 |
| WO | WO 98/20015 A1 | 5/1998 |
| WO | WO 98/22090 A1 | 5/1998 |
| WO | WO 98/29101 A1 | 7/1998 |
| WO | WO 98/42661 A1 | 10/1998 |
| WO | WO 99/00070 A1 | 1/1999 |
| WO | WO 99/01427 A2 | 1/1999 |
| WO | WO 99/18949 A1 | 4/1999 |
| WO | WO 99/22729 A1 | 5/1999 |
| WO | WO 99/33823 A1 | 7/1999 |
| WO | WO 99/37616 A1 | 7/1999 |
| WO | WO 99/44595 A2 | 9/1999 |
| WO | WO 99/44595 A3 | 9/1999 |
| WO | WO 99/51221 A1 | 10/1999 |
| WO | WO 99/67210 A1 | 12/1999 |
| WO | WO 99/67296 A1 | 12/1999 |
| WO | WO 00/03640 A1 | 1/2000 |
| WO | WO 00/06151 A1 | 2/2000 |
| WO | WO 00/30658 A1 | 6/2000 |
| WO | WO 00/33877 A1 | 6/2000 |
| WO | WO 00/56333 A1 | 9/2000 |
| WO | WO 00/59304 A1 | 10/2000 |
| WO | WO 00/76318 A1 | 12/2000 |
| WO | WO 01/12067 A1 | 2/2001 |
| WO | WO 01/15738 A2 | 3/2001 |
| WO | WO 01/15738 A3 | 3/2001 |
| WO | WO 01/26702 A2 | 4/2001 |
| WO | WO 01/26702 A3 | 4/2001 |
| WO | WO 01/45732 A2 | 6/2001 |
| WO | WO 01/45732 A3 | 6/2001 |
| WO | WO 01/70199 A1 | 9/2001 |
| WO | WO 01/85227 A2 | 11/2001 |
| WO | WO 01/85227 A3 | 11/2001 |
| WO | WO 01/89572 A1 | 11/2001 |
| WO | WO 02/17880 A2 | 3/2002 |
| WO | WO 02/17880 A3 | 3/2002 |
| WO | WO 02/17881 A2 | 3/2002 |
| WO | WO 02/17881 A3 | 3/2002 |
| WO | WO 02/20026 A2 | 3/2002 |
| WO | WO 02/20026 A3 | 3/2002 |
| WO | WO 02/32418 A1 | 4/2002 |
| WO | WO 02/34705 A2 | 5/2002 |
| WO | WO 02/43786 A2 | 6/2002 |
| WO | WO 02/43786 A3 | 6/2002 |
| WO | WO 02/47675 A1 | 6/2002 |
| WO | WO 02/051353 A2 | 7/2002 |
| WO | WO 02/056864 A2 | 7/2002 |
| WO | WO 02/056864 A3 | 7/2002 |
| WO | WO 02/056874 A2 | 7/2002 |
| WO | WO 02/056904 A1 | 7/2002 |
| WO | WO 02/151353 A3 | 7/2002 |
| WO | WO 02/070496 A1 | 9/2002 |
| WO | WO 02/076395 A2 | 10/2002 |
| WO | WO 02/076395 A3 | 10/2002 |
| WO | WO 03/004097 A1 | 1/2003 |
| WO | WO 03/006427 A1 | 1/2003 |
| WO | WO 03/015605 A2 | 2/2003 |
| WO | WO 03/015605 A3 | 2/2003 |
| WO | WO 03/017989 A1 | 3/2003 |
| WO | WO 03/026717 A1 | 4/2003 |
| WO | WO 03/030659 A1 | 4/2003 |
| WO | WO 03/041713 A1 | 5/2003 |
| WO | WO 03/047636 A2 | 6/2003 |
| WO | WO 03/047636 A3 | 6/2003 |
| WO | WO 03/080039 A1 | 10/2003 |
| WO | WO 03/092763 A1 | 11/2003 |
| WO | WO 03/095398 A2 | 11/2003 |
| WO | WO 03/095398 A3 | 11/2003 |
| WO | WO 2004/009066 A1 | 1/2004 |
| WO | WO 2004/011421 A1 | 2/2004 |
| WO | WO 2004/012874 A1 | 2/2004 |
| WO | WO 2004/037798 A1 | 5/2004 |
| WO | WO 2004/039313 A2 | 5/2004 |
| WO | WO 2004/039313 A3 | 5/2004 |
| WO | WO 2004/060283 A2 | 7/2004 |
| WO | WO 2004/064767 A2 | 8/2004 |
| WO | WO 2004/064767 A3 | 8/2004 |
| WO | WO 2004/098538 A2 | 11/2004 |
| WO | WO 2004/098538 A3 | 11/2004 |
| WO | WO 2005/003032 A1 | 1/2005 |
| WO | WO 2005/011575 A2 | 2/2005 |
| WO | WO 2005/011575 A3 | 2/2005 |
| WO | WO 2005/030118 A2 | 4/2005 |
| WO | WO 2005/030118 A3 | 4/2005 |
| WO | WO 2005/030135 A2 | 4/2005 |
| WO | WO 2005/030135 A3 | 4/2005 |
| WO | WO 2005/030147 A2 | 4/2005 |
| WO | WO 2005/030147 A3 | 4/2005 |
| WO | WO 2005/034860 A2 | 4/2005 |
| WO | WO 2005/034860 A3 | 4/2005 |
| WO | WO 2005/039664 A2 | 5/2005 |
| WO | WO 2005/039664 A3 | 5/2005 |
| WO | WO 2005/067986 A1 | 7/2005 |
| WO | WO 2005/070006 A2 | 8/2005 |
| WO | WO 2005/070006 A3 | 8/2005 |
| WO | WO 2005/070008 A2 | 8/2005 |
| WO | WO 2005/070008 A3 | 8/2005 |
| WO | WO 2005/070874 A1 | 8/2005 |
| WO | WO 2005/070883 A1 | 8/2005 |
| WO | WO 2005/072819 A1 | 8/2005 |
| WO | WO 2005/077962 A2 | 8/2005 |
| WO | WO 2005/077962 A3 | 8/2005 |
| WO | WO 2005/081752 A2 | 9/2005 |
| WO | WO 2005/081752 A3 | 9/2005 |
| WO | WO 2005/081964 A2 | 9/2005 |
| WO | WO 2005/094913 A1 | 10/2005 |
| WO | WO 2005/07384 A3 | 11/2005 |
| WO | WO 2005/0102282 A1 | 11/2005 |
| WO | WO 2005/107384 A2 | 11/2005 |
| WO | WO 2005/112954 A1 | 12/2005 |
| WO | WO 2005/115440 A2 | 12/2005 |
| WO | WO 2005/115440 A3 | 12/2005 |
| WO | WO 2005/120493 A1 | 12/2005 |
| WO | WO 2006/023693 A2 | 3/2006 |
| WO | WO 2006/023693 A3 | 3/2006 |
| WO | WO 2006/037105 A2 | 4/2006 |
| WO | WO 2006/037105 A3 | 4/2006 |
| WO | WO 2006/041855 A2 | 4/2006 |
| WO | WO 2006/041855 A3 | 4/2006 |
| WO | WO 2006/045639 A1 | 5/2006 |
| WO | WO 2006/055542 A2 | 5/2006 |
| WO | WO 2006/055542 A3 | 5/2006 |

(56) References Cited

FOREIGN PATENT DOCUMENTS

| | | |
|---|---|---|
| WO | WO 2006/058318 A2 | 6/2006 |
| WO | WO 2006/064056 A2 | 6/2006 |
| WO | WO 2006/066362 A1 | 6/2006 |
| WO | WO 2006/084909 A1 | 8/2006 |
| WO | WO 2006/084910 A1 | 8/2006 |
| WO | WO 2006/084911 A1 | 8/2006 |
| WO | WO 2006/084912 A1 | 8/2006 |
| WO | WO 2006/084913 A1 | 8/2006 |
| WO | WO 2006/084914 A1 | 8/2006 |
| WO | WO 2006/100155 A1 | 8/2006 |
| WO | WO 2006/095193 A2 | 9/2006 |
| WO | WO 2006/095193 A3 | 9/2006 |
| WO | WO 2006/096572 A1 | 9/2006 |
| WO | WO 2006/097348 A1 | 9/2006 |
| WO | WO 2006/099058 A2 | 9/2006 |
| WO | WO 2006/099058 A3 | 9/2006 |
| WO | WO 2006/100154 A1 | 9/2006 |
| WO | WO 2006/100156 A2 | 9/2006 |
| WO | WO 2006/100156 A3 | 9/2006 |
| WO | WO 2006/122960 A1 | 11/2006 |
| WO | WO 2006/122961 A1 | 11/2006 |
| WO | WO 2006/125016 A1 | 11/2006 |
| WO | WO 2006/125262 A1 | 11/2006 |
| WO | WO 2006/127591 A2 | 11/2006 |
| WO | WO 2006/127591 A3 | 11/2006 |
| WO | WO 2006/128121 A2 | 11/2006 |
| WO | WO 2006/128742 A2 | 12/2006 |
| WO | WO 2006/128742 A3 | 12/2006 |
| WO | WO 2006/128743 A1 | 12/2006 |
| WO | WO 2006/130982 A1 | 12/2006 |
| WO | WO 2007/003028 A1 | 1/2007 |
| WO | WO 2007/005910 A2 | 1/2007 |
| WO | WO 2007/005910 A3 | 1/2007 |
| WO | WO 2007/012165 A1 | 2/2007 |
| WO | WO 2007/016677 A2 | 2/2007 |
| WO | WO 2007/016677 A3 | 2/2007 |
| WO | WO 2007/023005 A1 | 3/2007 |
| WO | WO 2007/024501 A2 | 3/2007 |
| WO | WO 2007/024501 A3 | 3/2007 |
| WO | WO 2007/027859 A1 | 3/2007 |
| WO | WO 2007/028657 A1 | 3/2007 |
| WO | WO 2007/030266 A2 | 3/2007 |
| WO | WO 2007/030266 A3 | 3/2007 |
| WO | WO 2007/050379 A2 | 5/2007 |
| WO | WO 2007/050379 A3 | 5/2007 |
| WO | WO 2007/053292 A2 | 5/2007 |
| WO | WO 2007/053578 A2 | 5/2007 |
| WO | WO 2007/053578 A3 | 5/2007 |
| WO | WO 2007/054373 A1 | 5/2007 |
| WO | WO 2007/057763 A2 | 5/2007 |
| WO | WO 2007/057763 A3 | 5/2007 |
| WO | WO 2007/059311 A2 | 5/2007 |
| WO | WO 2007/059311 A3 | 5/2007 |
| WO | WO 2007/064895 A2 | 6/2007 |
| WO | WO 2007/064895 A3 | 6/2007 |
| WO | WO 2007/067477 A1 | 6/2007 |
| WO | WO 2007/084533 A2 | 7/2007 |
| WO | WO 2007/084533 A3 | 7/2007 |
| WO | WO 2007/086884 A2 | 8/2007 |
| WO | WO 2007/086884 A3 | 8/2007 |
| WO | WO 2007/088050 A2 | 8/2007 |
| WO | WO 2007/088050 A3 | 8/2007 |
| WO | WO 2007/088123 A2 | 8/2007 |
| WO | WO 2007/088123 A3 | 8/2007 |
| WO | WO 2007/092284 A2 | 8/2007 |
| WO | WO 2007/092284 A3 | 8/2007 |
| WO | WO 2007/100910 A2 | 9/2007 |
| WO | WO 2007/100910 A3 | 9/2007 |
| WO | WO 2007/103190 A2 | 9/2007 |
| WO | WO 2007/103190 A3 | 9/2007 |
| WO | WO 2007/127725 A2 | 11/2007 |
| WO | WO 2007/127725 A3 | 11/2007 |
| WO | WO 2007/133922 A2 | 11/2007 |
| WO | WO 2007/133922 A3 | 11/2007 |
| WO | WO 2007/143185 A2 | 12/2007 |
| WO | WO 2007/143185 A3 | 12/2007 |
| WO | WO 2007/149437 A1 | 12/2007 |
| WO | WO 2007/149520 A2 | 12/2007 |
| WO | WO 2007/149520 A3 | 12/2007 |
| WO | WO 2008/005313 A2 | 1/2008 |
| WO | WO 2008/005313 A3 | 1/2008 |
| WO | WO 2008/013633 A2 | 1/2008 |
| WO | WO 2008/013633 A3 | 1/2008 |
| WO | WO 2008/020218 A1 | 2/2008 |
| WO | WO 2008/027203 A2 | 3/2008 |
| WO | WO 2008/027203 A3 | 3/2008 |
| WO | WO 2008/062160 A1 | 5/2008 |
| WO | WO 2008/071242 A1 | 6/2008 |
| WO | WO 2008/088507 A2 | 7/2008 |
| WO | WO 2008/088507 A3 | 7/2008 |
| WO | WO 2008/095841 A2 | 8/2008 |
| WO | WO 2008/095841 A3 | 8/2008 |
| WO | WO 2008/098192 A2 | 8/2008 |
| WO | WO 2008/098192 A3 | 8/2008 |
| WO | WO 2008/100591 A2 | 8/2008 |
| WO | WO 2008/100591 A3 | 8/2008 |
| WO | WO 2008/112391 A2 | 9/2008 |
| WO | WO 2008/112391 A3 | 9/2008 |
| WO | WO 2008/116497 A1 | 10/2008 |
| WO | WO 2008/116925 A1 | 10/2008 |
| WO | WO 2008/130567 A1 | 10/2008 |
| WO | WO 2008/141416 A1 | 11/2008 |
| WO | WO 2008/150505 A1 | 12/2008 |
| WO | WO 2008/157393 A1 | 12/2008 |
| WO | WO 2009/014616 A1 | 1/2009 |
| WO | WO 2009/014829 A2 | 1/2009 |
| WO | WO 2009014829 A3 | 1/2009 |
| WO | WO 2009/019498 A2 | 2/2009 |
| WO | WO 2009/019498 A3 | 2/2009 |
| WO | WO 2009/019499 A2 | 2/2009 |
| WO | WO 2009/026680 A1 | 3/2009 |
| WO | WO 2009/036571 A1 | 3/2009 |
| WO | WO 2009/049208 A1 | 4/2009 |
| WO | WO 2009/064861 A2 | 5/2009 |
| WO | WO 2009/064861 A3 | 5/2009 |
| WO | WO 2009/073643 A2 | 6/2009 |
| WO | WO 2009/073643 A3 | 6/2009 |
| WO | WO 2009/073940 A2 | 6/2009 |
| WO | WO 2009/073940 A3 | 6/2009 |
| WO | WO 2009/080795 A1 | 7/2009 |
| WO | WO 2009/086470 A2 | 7/2009 |
| WO | WO 2009/086470 A3 | 7/2009 |
| WO | WO 2009/088433 A1 | 7/2009 |
| WO | WO 2009/098113 A1 | 8/2009 |
| WO | WO 2009/117182 A2 | 9/2009 |
| WO | WO 2009/117182 A3 | 9/2009 |
| WO | WO 2009/117183 A1 | 9/2009 |
| WO | WO 2009/124379 A1 | 10/2009 |
| WO | WO 2009/131931 A1 | 10/2009 |
| WO | WO 2009/155689 A1 | 12/2009 |
| WO | WO 2009/155690 A1 | 12/2009 |
| WO | WO 2010/002450 A2 | 1/2010 |
| WO | WO 2010/002450 A3 | 1/2010 |
| WO | WO 2010/033242 A2 | 3/2010 |
| WO | WO 20100333242 A3 | 3/2010 |
| WO | WO 2010/045415 | 4/2010 |
| WO | WO 2010/045465 A1 | 4/2010 |
| WO | WO 2010/048724 A1 | 5/2010 |
| WO | WO 2010/080213 A2 | 7/2010 |
| WO | WO 2010/080213 A3 | 7/2010 |
| WO | WO 2010/096320 A2 | 8/2010 |
| WO | WO 2010/096320 A3 | 8/2010 |
| WO | WO 2010/114669 A1 | 10/2010 |
| WO | WO 2010/120414 A2 | 10/2010 |
| WO | WO 2010/151505 A1 | 12/2010 |
| WO | WO 2011/022652 A1 | 2/2011 |

OTHER PUBLICATIONS

Barraud, N., et al., "Involvement of Nitric Oxide in Biofilm Dispersal of *Pseudomonas aeruginosa*," *Journal of Bacteriology*, 2006, vol. 188(21), pp. 7344-7353.

(56) References Cited

OTHER PUBLICATIONS

Bohl Masters et al. "Effects of nitric oxide releasing vinyl poly(vinyl alcohol) hydrogel dressings on dermal wound healing in diabetic mice", *Wound Repair and Regeneration* 10(5):286-294 (2002).
Brennan et al., "The Role of Nitric Oxide in Oral Diseases", *Archives of Oral Biology*, 2003, vol. 48, pp. 93-100.
Coban, A., et al., "The Effect of Nitric Oxide Combined with Fluoroquinolones against *Salmonellaenterica* Serovar Typhimurium in Vitro," *Mem Inst Oswaldo Cruz*, Rio de Janeiro, 2003, vol. 98(3), pp. 419-423.
Gupta, R., et al., "Bioactive materials for biomedical applications using sol-gel technology," *Biomed Mater.*, 2008, Vol. 3, pp. 1-15.
Hetrick et al. "Anti-biofilm efficacy of nitric oxide-releasing silica nanoparticles", *Biomaterials* 30:2782-2789 (2009).
Hetrick et al., "Bactericidal Efficacy of Nitric Oxide-Releasing Silica Nanoparticles," *Acsnano*, 2008, vol. 2(2), pp. 235-246.
Hrabie et al., "Chemistry of the nitric oxide-releasing diazeniumdiolate ("nitrosohydroxylamine") functional group and its oxygen-substituted derivatives," *Chem Rev.* 2002, 102, p. 1135-1154.
International Search Report and Written Opinion for corresponding PCT application No. PCT/US2009/005643, Date of Mailing May 24, 2010.
Iwakir, N. et al., Synthesis of Amphiphillic polysiloxanes and their properties for formation of nano-aggregates, *Colloid Polym Sci*, 2009; 287: 577-582.
Living Water Acid-Alkaline Balance http://www.livingwaterhealthsolutions.com/Articles/alkalize.php Accessed online Nov. 3, 2011.
McElhaney-Feser, G., et al., "Synergy of Nitric Oxide and Azoles against *Candida* Species in Vitro," *Antimicrobial Agents and Chemotherapy*, 1998, vol. 42(9), pp. 2342-2346.
Notification of Transmittal of the International Search Report and the Written Opinion of the International Searching Authority, or the Declaration corresponding to International Application No. PCT/US2010/046173 mailed Dec. 6, 2010.
Notification Concerning Transmittal of International Preliminary Report on Patentability for corresponding PCT Application No. PCT/US2009/005643, mailed Apr. 28, 2011.
Notification of the Transmittal of the International Search Report and the Written Opinion of the. International Searching Authority, or the Declaration; International Search Report; Written Opinion of the International Search authority corresponding to PCT/US2010/046209; mailed May 23, 2011; 13 pages.
Notification of the Transmittal of the International Search Report and the Written Opinion of the International Searching Authority, or the Declaration; International Search Report; Written Opinion of the International Searching Authority corresponding to PCT/US2010/052460; Mailed Jan. 24, 2011; 10 pages.
Notification Concerning Transmittal of International Preliminary Report on Patentability (Chapter 1 of The Patent Cooperation Treaty) corresponding to PCT/US2010/046173; mailed Mar. 1, 2012.
Robson, MC, "Wound Infection, A Failure of Wound Healing Caused by an Imbalance of Bacteria," *Surg Clin North Amer*, 1997, Jun; 77(3): 637-50.
Saaral, NY, "The Equilibrium Between Endothelin-1/Nitric Oxide in Acne Vulgaris," *Istanbul Tip Fakultesi Dergisi Cilt*, 2008, 71(4).
Salivary pH Testing https://allicincenter.com/pdf/ph_testing.pdf Accessed online Nov. 3, 2011.
Sato, EF et al., *J. Clin. Biochem. Nutr.* (Pub Online Dec. 28, 2007), 42; pp. 8-13.
Schaffer, MR, et al., "Diabetes-impaired healing and reduced wound nitric oxide synthesis: a possible pathophysiologic correlation". *Surgery*, May 1997; 121(5):513-9.
Shi, HP, et al., "The role of iNOS in wound healing". *Surgery*, vol. 130, Issue 2, Aug. 2001; pp. 225-229.
Slowing, I.I., et al. *Adv. Drug Del. Rev.* (Aug. 2008), 60; pp. 1278-1288.
Stasko, N., et al., "Dendrimers as a Scaffold for Nitric Oxide Release," *J. Am. Chem Soc.*, 2006, vol. 128, pp. 8265-8271.
Summersgill, J., et al., "Killing of *Legionella pneumnophila* by nitric oxide in γ-interferon-activated macrophages," *Journal of Leukocyte Biology*, 1992, vol. 52, p. 625-629.
Tang, X., et al., "Synthesis of Beta-Lactamase Activated Nitric Oxide Donors," *Biorgania & Medicinal Chemistry Letters*, 2003, vol. 13, pp. 1687-1690.
Zhu, D., et al., "Corrosion protection of metals by water-based silane mixtures of bis-[trimethosysilylpropyl]amine and vinyltriacetoxysilane," *Progress in Organic Coatings*, 2004, vol. 49, pp. 42-53.
Jobgen et al. "Regulatory role for the arginine-nitric oxide pathway in metabolism of energy substrates", *J. Nutritional Biochemistry* 17:571-588 (2006).
Thiboutot et al. "Human Skin is a Steroidogenic Tissue: Steroidogenic Enzymes and Cofactors are Expressed in Epidermis, Normal Sebocytes, and an Immortalized Sebocyte Cell Line (SEB-1)", *J. Investigative Dermatology* 120:905-914 (2003).
Rosignoli et al. "Involvement of the SREBP pathway in the mode of action of androgens in sebaceous glands in vivo", *Experimental Dermatology* 12:480-489 (2003).
Yatera et al. "Severe dyslipidaemia, atherosclerosis, and sudden cardiac death in mice lacking all NO synthases fed a high-fat diet", *Cardiovascular Research* 87:675-682 (2010).
Pomertantz et al. "Nitric Oxide is a Mediator of the Inhibitory Effect of Activated Macrophages on Production of Androgen by the Leydig Cell of the Mouse", *Endocrinology* 319(3):922-931 (1998).
U.S. Appl. No. 13/256,928, filed Oct. 4, 2011, Stasko et al.
Lamanna et al. "D-Aspartic acid and nitric oxide as regulators of androgen production in boar testis", *Theriogenology* 67:249-254 (2007).
Gharavi et al. "Role of Endothelial Nitric Oxide Synthase in the Regulation of SREBP Activation by Oxidized Phospholipids", *Circ. Res.* 98:768-776 (2006).
Pawin et al. "Physiopathology of acne vulgaris: recent data, new understanding of the treatments", *Eur. J. Dermatol.* 14:4-12 (2004).
Smith et al. "Sebaceous gland lipids: friend or foe?" *J. Lipid Research* 49:271-281 (2008).
Thiboutot et al. "New insights into the management of acne: An update from the Global Alliance to Improve Outcomes in Acne Group", *J. Am. Acad. Dermatol.* 60:S1-S50 (2009).
Bellew et al. "Pathogenesis of Acne Vulgaris: What's New, What's Interesting and What May Be Clinically Relevant", *J. Drugs Dermatol.* 10(6):582 (2011).
Thiboutot "New Treatments and Therapeutic Strategies for Acne", *Arch Fam Med* 9:179-187 (2000).
Notification of Transmittal of the International Search Report and the Written Opinion of the International Searching Authority, or the Declaration corresponding to International Application No. PCT/US2011/065043 mailed Apr. 24, 2012.
Notification of Transmittal of the International Search Report and the Written Opinion of the International Searching Authority, or the Declaration corresponding to International Application No. PCT/US2011/045384 mailed Nov. 5, 2012.
Notification of Transmittal of the International Search Report and the Written Opinion of the International Searching Authority, or the Declaration corresponding to PCT/US2012/45390 mailed Dec. 11, 2012.
International Search Report and Written Opinion Corresponding to International Application No. PCT/US 13/28215; Date of Mailing: Apr. 29, 2013; 17 Pages.
Alsantali A. et al., "Androgens and hair loss", *Current Opinion in Endocrinology, Diabetes & Obesity*, 2009, 16:246-253.
Ashutosh K. et al., "Use of nitric oxide inhalationin chronic obstructive pulmonary disease", *Thorax*, 2000; 55:109-113.
Azizzadeh B. et al., "Nitric Oxide Improve Cisplatin Cytotoxicity in Head and Neck Squamous Cell Carcinoma", *Laryngoscope*, 111: Nov. 2001, pp. 1896-1900.
Barst R.J. et al., "Clinical perspectives with long-term pulsed inhaled nitric oxide for the treatment of pulmonary arterial hypertension", *Pulmonary Circulation*, Apr.-Jun. 2012, vol. 2, No. 2, pp. 139-147.
Benthin G. et al., "Transformation of subcutaneous nitric oxide into nitrate in the rat", *Biochem. J.*, 1997, 323, 853-858.

(56) References Cited

OTHER PUBLICATIONS

Benz S. et al., "Effect of Nitric Oxide in Ischemia/Reperfusion of the Pancreas", *Journal of Surgical Research*, vol. 106, Issue 1, pp. 46-53, Jul. 2002.

Bian K. et al., "Vascular System: Role of Nitric Oxide in Cardiovascular Diseases", *The Journal of Clinical Hypertension*, vol. 10, No. 4, Apr. 2008, pp. 304-310.

Bloch K.D. et al. "Inhaled NO as a therapeutic agent", *Cardiovascular Research*, 75, 2007, 339-348.

Bonavida B. et al., "Novel therapeutic applications of nitric oxide donors in cancer: Roles in chemo- and immunosensitization to apoptosis and inhibition of metastases", *Nitric Oxide*, vol. 19, Issue 2, Sep. 2008, pp. 152-157.

Bonavida B. et al., "Therapeutic potential of nitric oxide in cancer", *Drug Resist Updat.*, 2006, Jun.; 9(3):157-73, Epub Jul. 5, 2006.

Boykin J.V. et al., "HBO mediates increased nitric oxide production associated with wound healing", *Wound Repair and Regeneration*, vol. 12, No. 2, Mar.-Apr. 2004.

Boykin Jr. J.V., "Wound Nitric Oxide Bioactivity: A Promising Diagnostic Indicator for Diabetic Foot Ulcer Management", *Journal of Wound, Ostomy & Continence Nursing*, Jan./Feb. 2010, vol. 37, Issue 1, p. 25-32.

Bruch-Gerharz D. et al., "Nitric Oxide in Human Skin: Current Status and Future Prospects", *J. Inves Dermatol*, 110:1-7, 1998.

Cals-Grierson M.M. et al., "Nitric oxide function in the skin", *Nitric Oxide*, vol. 10, Issue 4, Jun. 2004, pp. 179-193.

Carlsson S. et al., "Intravesical Nitric Oxide Delivery for Prevention of Catheter-Associated Urinary Tract Infections", *Antimicrob. Agents Chemother.* 2005, 49(6):2352.

Chen W. et al., "Cutaneous Androgen Metabolism: Basic Research and Clinical Perspectives", *J. Invest Dermatol*, 119:992-1007, 2002.

De Groote M.A. et al., "NO Inhibitions: Antimicrobial Properties of Nitric Oxide", *Clinical Infectious Diseases*, 1995, 21 (Supplement 2), S162-S165.

Deeb R.S. et al., "Inducible Nitric Oxide Synthase Mediates Prostaglandin $H_2$ Synthase Nitration and Suppresses Eicosanoid Production", *American Journal of Pathology*, vol. 168, No. 1, Jan. 2006, 349-362.

Del Punta K. et al., "Nitric Oxide Inhibits Leydig Cell Steroidogenesis", *Endocrinology*, vol. 137, No. 12, 1996, 5337-5343.

Di Costanzo L. et al., "Crystal Structure of Human Liver $\Delta^4$-3-Ketosteroid 5β-Reductase (AKR1D1) and Implications for Substrate Binding and Catalysis", *The Journal of Biological Chemistry*, vol. 283, No. 24, pp. 16830-16839, Jun. 13, 2008.

Drewett J.G. et al., "Nitric oxide potently inhibits the rate-limiting enzymatic step I steroidogenesis", *Molecular and Cellular Endocrinology*, 194, (2002), 39-50.

European Search Report Corresponding to European Patent Application No. 09820905.9; Dated: Feb. 14, 2013; 7 Pages.

Fang F., "Mechanisms of Nitric Oxide-related Antimicrobial Activity", *J.Clin. Invest.*, vol. 99, No. 12, Jun. 1997, 2818-2825.

Frederiksen L.J. et al., "Chemosensitization of Cancer In vitro and In vivo by Nitric Oxide Signaling", *Clin Cancer Res.* 2007; 13:2199-2206.

Fritsch M. et al., "Sebocytes are the Key Regulators of Androgen Homeostasis in Human Skin", *J. Invest Dermatol*, 116:793-800, 2001.

Garza L. et al., "Bald scalp in men with androgenetic alopecia retains hair follicle stem cells but lacks CD200-rich and CD34-positive hair follicle progenitor cells", *The Journal of Clinical Investigation*, vol. 121, No. 2, Feb. 2011, 613-622.

Ghaffari A. et al., "Potential application of gaseous nitric oxide as a topical antimicrobial agent", *Nitric Oxide*, vol. 14, Issue 1, Feb. 2006, pp. 21-29.

Goodwin D.C. et al., "Effects of nitric oxide and nitric oxide-derived species on prostaglandin endoperoxide synthase and prostaglandin biosynthesis", *FASEB J.*, 13, 1121-1136, 1999.

Goodwin D.C. et al., "Nitric Oxide Trapping of Tyrosyl Radicals Generated during Prostaglandin Endoperoxide Synthase Turnover", *The Journal of Biological Chemistry*, vol. 273, No. 15, Apr. 10, 1998, pp. 8903-8909.

Griffin J.E. et al., "The Androgen Resistance Syndromes: 5α-Reductase Deficiency, Testiclular Feminization, and Related Disorders", *The Metabolic Basis Of Inherited Disease II*, Sixth Edition, 1989, McGraw-Hill, New York 1919-1944.

Hamilton J.B., "Male Hormone Stimulation Is Prerequisite And An Incitant In Common Baldness", *Am. J. Anat.*, 1942, 71, 451-480.

Herman a.G. et al., "Therapeutic potential of nitric oxide donors in the prevention and treatment of atherosclerosis", *European Heart Journal*, 2005, 26, 1945-1955.

Hirst D. et al., "Targeting nitric oxide for cancer therapy", *Journal of Pharmacy and Pharmacology*, 2007, 59:3-13.

Howlin R. et al., "Nitric oxide-mediated dispersal and enhanced antibiotic sensitivity in *pseudomonas aeruginosa* biofilms from the cystic fibrosis lung", *Archives of Disease In Childhood*, 2011; 96:A45.

Huerta S. et al., "Nitric oxide donors: Novel cancer therapeutics (Review)", *International Journal of Oncology*, 33, 909-927, 2008.

Imperato-McGinley, J. et al., "The Androgen Control of Sebum Production. Studies of Subjects With Dihydrotestosterone Deficiency and Complete Androgen Insensitivity", *Journal of Endocrinology and Metabolism*, vol. 76, No. 2, 1993, 524-528.

Johnson T. A. et al., "Reduced ischemia/reperfusion injury via glutathione-initiated nitric oxide-releasing dendrimers", *Nitric Oxide*, 2009, 7 Pages.

Jones M.L. et al., "Antimicrobial properties of nitric oxide and its application in antimicrobial formulations and medical devices", *Appl Microbiol Biotechnol*, 2010, 88:401-407.

Kelce W. et al., "Persistent DDT metabolite p,p'-DDE is a potent androgen receptor antagonist", *Nature*, vol. 375, Jun. 15, 1995, 581-585.

Kiziltepe T. et al., "JS-K, a GST-activated nitric oxide generator, induces DNA double-strand breaks, activates DNA damage response pathways, and induces apoptosis in vitro and in vivo in human multiple myeloma cells", *Blood*, 2007, 110:709-718.

Lamas S. et al., "Nitric oxide signaling comes of age: 20 years and thriving", *Cardiovascular Research*, 75, 2007, 207-209.

Liu X. et al., "Nitric Oxide Inhalation Improves Microvascular Flow and Decreases Infarction Size After Myocardial Ischemia and Reperfusion", *Journal of the American College of Cardiology*, vol. 50, No. 8, 2007.

Luo J. et al., "Nitric oxide: a newly discovered function on wound healing", *Acta Pharmacologica Sinica*, Mar. 2005; 26 (3):259-264.

McGrowder D. et al., "Therapeutic Uses of Nitric Oxide-donating Drugs in the Treatment of Cardiovascular Diseases", *International Journal of Pharmacology*, 2(4):366-373, 2006.

Minamiyama Y. et al., "Irreversible Inhibition of Cytochrome P450 by Nitric Oxide", *J. Pharmacol. Exp. Ther.*, 1997, vol. 283, No. 3, 1479-1485.

Morgan E.T. et al., "Cytochromes P450 and Flavin Monooxygenases-Targets And Sources Of Nitric Oxide", *Drug Metab. Dispos.*, 29:1366-1376, 2001.

Napoli C. et al., "Nitric oxide and atherosclerosis: An update", *Nitric Oxide*, vol. 15, Issue 4, Dec. 2006, pp. 265-279.

Phillips L. et al., "Nitric Oxide Mechanism of Protection in Ischemia and Reperfusion Injury", *Journal of Investigative Surgery*, 22, 46-55, 2009.

Pomerantz D. et al., "Nitric Oxide Is A Mediator of the Inhibitory Effect of Activated Macrophages on Production of Androgen by the Leydig Cell of the Mouse", *Endocrinology*, 139:922-931, 1998.

Puerto A.M. et al., "Regional scalp differences of the androgenic metabolic pattern in subjects affected by male pattern baldness", *Rev. Esp. Fisiol.*, 1990, 46(3), 289-296.

Roediger W. et al., "Inhibition of Hepatocyte Lipogenesis by Nitric Oxide Donor: Could Nitric Oxide Regulate Lipid Synthesis?", *IUBMB Life*, 56(1):35-40, Jan. 2004.

Saavedra J.E. et al., "Esterase-Sensitive Nitric Oxide Donors of the Diazeniumdiolate Family: In Vitro Antileukemic Activity", *J. Med. Chem.* 2000, 43, 261-269.

(56) References Cited

OTHER PUBLICATIONS

Sansone G. et al., "Differential Rates Of Conversion Of Testosterone To Dihydrotestosterone in Acne And In Normal Human Skin—A Possible Pathogenic Factor In Acne", *J. Invest.Dermatol.*, 1971, vol. 56, 366-372.

Schäffer M.R. et al., "Diabetes-impaired healing and reduced wound nitric oxide synthesis: A possible pathophysiologic correlation", *Surgery*, vol. 121, Issue 5, pp. 513-519, May 1997.

Schairer D.O. et al., "The potential of nitric oxide releasing therapies as antimicrobial agents", *Virulence*, 3:3, 271-279; May/Jun. 2012.

Schulz R. et al., "Nitric oxide in myocardial ischemia/reperfusion injury", *Cardiovascular Research*, 61, 2004, 402-413.

Schwentker A. et al., "Nitric oxide and wound repair: role of cytokines?" *Nitric Oxide*, vol. 7, Issue 1, Aug. 2002, pp. 1-10.

Simeone A.M. et al., "N-(4-Hydroxyphenyl) retinamide and nitric oxide pro-drugs exhibit apoptotic and anti-invasive effects against bone metastatic breast cancer cells" *Carcinogenesis*, vol. 27, No. 3, pp. 568-577, 2006.

Siriussawakul A. et al. "Role of nitric oxide in hepatic ischemia-reperfusion injury", *World Journal of Gastroenterology*, Dec. 28, 2010, 16(48):6079-6086.

Smith K. et al., "Sebaceous gland lipids: friend or foe?", *J. Lipid Res.* 2008, 49, 271-281.

Snyder G. et al., "Nitric Oxide Inhibits Aromatase Activity: Mechanisms of Action", *J. Steroid Biochem. Molec. Biol.*, vol. 58, No. 1, p. 63-69, 1996.

Stevens E.V. et al., "Nitric Oxide-Releasing Silica Nanoparticle Inhibition of Ovarian Cancer Cell Growth", *Molecular Pharmaceutics*, vol. 7, No. 3, 775-785, 2010.

Terpolilli N.A. et al., "Inhalation of Nitric Oxide Prevents Ischemic Brain Damage in Experimental Stroke by Selective Dilatation of Collateral Arterioles", *Circulation Research*, 2012; 110:727-738.

Thiboutot D., "New Treatments and Therapeutic Strategies for Acne", *Arch Fam Med*. 2000; 9:179-187.

Thomas D.D. et al., "Hypoxic inducible factor $1\alpha$, extracellular signal-regulated kinase, and p53 are regulated by distinct threshold concentrations of nitric oxide", *PNAS*, Jun. 15, 2004, vol. 101, No. 24, 8894-8899.

Weller R. "Nitric oxide donors and the skin: useful therapeutic agents?" *Clinical Science*, 2003, 105, 533-535.

Wink D.A. et al., "The multifaceted roles of nitric oxide in cancer", *Carcinogenesis*, vol. 19, No. 5, pp. 711-721, 1998.

Witte M.B. et al., "Nitric oxide enhances experimental wound healing in diabetes", *British Journal of Surgery*, 2002, 89, 1594-1601.

Witte M.B. et al., "Role of nitric oxide in wound repair", *The American Journal of Surgery*, vol. 183, Issue 4, pp. 406-412, Apr. 2002.

Wong C. et al., "Androgen Receptor Antagonist versus Agonist Activities of the fungicide Vinclozolin relative to Hydroxyflutamide", *J. Biol. Chem.*, 1995, vol. 270, No. 34, pp. 19998-20003.

Yetik-Anacak G. et al., "Nitric oxide and the endothelium: History and impact on cardiovascular disease", *Vascular Pharmacology*, vol. 45, Issue 5, Nov. 2006, pp. 268-276.

Zhang H. et al., "Nitric Oxide-Releasing Fumed Silica Particles: Synthesis, Characterization, and Biomedical Application", *J. Am. Chem. Soc.*, 2003, 125, 5015-5024.

Zhu H. et al., "Effects of Nitric Oxide on Skin Burn Wound Healing", *Journal of Burn Care & Research*, Sep./Oct. 2008, vol. 29, Issue 5, pp. 804-814.

Zhu H. et al., "Nitric Oxide Accelerates the Recovery from Burn Wounds", *World Journal of Surgery*, 2007, 31:624-631.

International Preliminary Report on Patentability Corresponding to International Application No. PCT/US2011/065043; Date of Mailing: Jun. 27, 2013; 5 pages.

\* cited by examiner

METHODS OF DECREASING SEBUM PRODUCTION IN THE SKIN

CROSS-REFERENCE TO RELATED APPLICATIONS

This application claims priority from U.S. Provisional Application Ser. No. 61/423,292, filed Dec. 15, 2010, and U.S. Provisional Application No. 61/504,634, filed Jul. 5, 2011, the disclosure of each of which is hereby incorporated by reference herein in its entirety.

FIELD OF THE INVENTION

The present invention is directed to methods of treating dermatological ailments. More particularly, the present invention is directed to methods of reducing sebum production in the skin.

BACKGROUND OF THE INVENTION

Acne vulgaris is the most common skin disease in the United States. It is estimated that 40 to 50 million Americans have acne, including 80% of people between the ages of 11 and 30. The annual direct costs associated with the treatment of acne exceeded $2.8 billion in 2007, with the majority of those costs attributable to prescription drugs. In addition, acne causes both physical and psychological effects, including permanent scarring, anxiety, depression, and poor self-esteem. Even in cases of mild acne, the social stigma associated with the disease frequently results in significant emotional distress and other psychological issues. Due to its social impact, frequency of recurrence or relapse, and necessary maintenance over a prolonged course of therapy, the American Academy of Dermatologists have recommend that acne vulgaris be re-classified and investigated as a chronic disease.

Acne vulgaris results from the complex interplay of four major pathogenic factors: 1) overproduction of sebum by the sebaceous gland; 2) abnormal keratinization in the follicle; 3) colonization of the hair follicles by the anaerobic, lipophilic bacterium *Propionibacterium acnes*, or *P. acnes*; and 4) release of inflammatory mediators into the skin.

The role of over sebum production in the pathogenesis of acne has been studied. See, Bellew et al. "Pathogenesis of Acne Vulgaris: What's new, What's interesting, and What may be clinically relevant," *J. Drugs Dermatol.* 2011; 10, 582-585, the disclosure of which is incorporated by reference, as is set forth in its entirety herein. All acne lesions begin when the combination of excess sebum and abnormal epithelial desquamation clog up a follicle, forming a microscopic lesion known as a microcomedo. The aneaerobic, lipid-rich environment of the microcomedo provides an ideal location for *P. acnes* proliferation. Each microcomedo can progress to form a non-inflammatory open or closed comedone (commonly referred to as a "blackhead" or "whitehead," respectively), or an inflammatory lesion that can be further categorized as a papule, pustule, nodule, or cyst.

The complexity of the disease may require multiple treatments that may span oral and topical antimicrobials, oral and topical retinoids, oral contraceptives and other prescription skin cleansers. The most effective therapies for acne are those that can safely address more than one of the major causes of acne pathogenesis.

Antibiotics were the first successful acne treatment due to their antimicrobial and anti-inflammatory properties. Both topical and systemic antibiotics have been very successful, but the protracted treatment periods required have led to the development of resistance of *P. acnes* and in other non-targeted (and potentially pathogenic) commensal organisms. Combining antibiotics with topical retinoids targets three of the four major pathogenic factors associated with acne (all but sebum production). The oral retinoid isotretinoin (e.g., Accutane®) is the only drug known to affect all four pathogenic factors associated with acne. However, the severity of its potential side effects (known teratogen and linked to depression, psychosis and suicide) has limited its use and led to numerous lawsuits.

While the problems associated with isotretinoin are the most severe, all of the current acne medications have some adverse effects. The majority of topical treatments lead to dryness, irritation and peeling of the skin, and oral antibiotics may cause gastrointestinal tract irritation, photosensitivity of skin, headache, dizziness, anemia, bone and joint pain, nausea and/or depression. As such, new medications for the treatment of acne are desired, and particularly new treatments that target sebum production.

SUMMARY OF THE INVENTION

Provided herein according to embodiments of the invention are methods of decreasing sebum production in skin of a subject. Such methods include applying nitric oxide and/or at least one nitric oxide source to the skin in an amount sufficient to decrease sebum production and/or decrease, eliminate or prevent acne. In some embodiments of the invention, gaseous nitric oxide is applied to the skin of the subject. In some embodiments of the invention, at least one nitric oxide source is applied to the skin of the subject.

In some embodiments, the at least one nitric oxide source includes a nitric oxide (NO)-releasing compound, including small molecule NO-releasing compounds and macromolecular NO-releasing compounds. In some embodiments, the NO-releasing compounds include N-diazeniumdiolate-functionalized compounds, and in some embodiments, the N-diazeniumdiolate-functionalized compounds include N-diazeniumdiolate co-condensed polysiloxane macromolecules. In some embodiments, the NO-releasing compounds include nitrosothiol-functionalized compounds. In some embodiments, the NO-releasing compound is present in a pharmaceutically acceptable composition, and in some embodiments, the pharmaceutically acceptable composition includes at least one other therapeutic agent.

Also provided herein according to embodiments of the invention are methods of decreasing sebum production in skin of a subject that include systemically applying nitric oxide and/or at least one nitric oxide source to the subject in an amount sufficient to decrease sebum production and/or decrease, eliminate or prevent acne in the skin.

DETAILED DESCRIPTION OF EMBODIMENTS OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

All patents, patent applications and publications referred to herein are incorporated by reference in their entirety. In the event of conflicting terminology, the present specification is controlling.

The embodiments described in one aspect of the present invention are not limited to the aspect described. The embodiments may also be applied to a different aspect of the invention as long as the embodiments do not prevent these aspects of the invention from operating for its intended purpose.

Chemical Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-5}$ straight-chain alkyls. In other embodiments, "alkyl" refers, in particular, to $C_{1-5}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR$^1$R", wherein R$^1$ and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, f-butoxyl, and pentoxyl. The term "oxyalkyl" can be used interchangeably with "alkoxyl". In some embodiments, the alkoxyl has 1, 2, 3, 4, or 5 carbons.

"Aralkyl" refers to an aryl-alkyl group wherein aryl and alkyl are as previously described, and included substituted aryl and substituted alkyl. Exemplary aralkyl groups include benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

"Arylene" refers to a bivalent aryl group. An exemplary arylene is phenylene, which can have ring carbon atoms available for bonding in ortho, meta, or para positions with regard to each other, i.e., respectively. The arylene group can also be napthylene. The arylene group can be optionally substituted (a "substituted arylene") with one or more "aryl group substituents" as defined herein, which can be the same or different.

"Aralkylene" refers to a bivalent group that contains both alkyl and aryl groups. For example, aralkylene groups can have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as $NR_3$, $NH_3$, $NHR_2$, and $NH_2R$, wherein R can be alkyl, branched alkyl, cycloalkyl, aryl, alkylene, arylene, aralkylene. Thus, "amino" as used herein can refer to a primary amine, a secondary amine, or a tertiary amine. In some embodiments, one R of an amino group can be a cation stabilized diazeniumdiolate (i.e., $NONO^-X^+$).

The terms "cationic amine" and "quaternary amine" refer to an amino group having an additional (i.e., a fourth) group, for example a hydrogen or an alkyl group bonded to the nitrogen. Thus, cationic and quarternary amines carry a positive charge.

The term "alkylamine" refers to the -alkyl-$NH_2$ group.

The term "carbonyl" refers to the —(C=O)— group.

The term "carboxyl" refers to the —COOH group and the term "carboxylate" refers to an anion formed from a carboxyl group, i.e., —$COO^-$.

The terms "halo", "halide", or "halogen" as used herein refer to fluoro, chloro, bromo, and iodo groups.

The term "hydroxyl" and "hydroxy" refer to the —OH group.

The term "hydroxyalkyl" refers to an alkyl group substituted with an —OH group.

The term "mercapto" or "thio" refers to the —SH group. The term "silyl" refers to groups comprising silicon atoms (Si).

As used herein the term "alkoxysilane" refers to a compound comprising one, two, three, or four alkoxy groups bonded to a silicon atom. For example, tetraalkoxysilane refers to $Si(OR)_4$, wherein R is alkyl. Each alkyl group can be the same or different. An "alkylsilane" refers to an alkoxysilane wherein one or more of the alkoxy groups has been replaced with an alkyl group. Thus, an alkylsilane comprises at least one alkyl-Si bond. The term "fluorinated silane" refers to an alkylsilane wherein one of the alkyl groups is substituted with one or more fluorine atoms. The term "cationic or anionic silane" refers to an alkylsilane wherein one of the alkyl groups is further substituted with an alkyl substituent that has a positive (i.e., cationic) or a negative (i.e. anionic) charge, or can become charged (i.e., is ionizable) in a particular environment (i.e., in vivo).

The term "silanol" refers to a Si—OH group.

Methods of Decreasing Sebum Production in Skin

Provided according to some embodiments of the invention are methods of decreasing sebum production that include applying nitric oxide and/or at least one nitric oxide source to skin of a subject to decrease sebum production in the skin. While not being limited to any particular theory, it is postulated that sebum production may be reduced by nitric oxide through one or more of reducing the size or number of sebum production sites (i.e. decreasing the size of the sebaceous glands or effecting direct sebocyte toxicity) or through biochemical regulation of lipogenesis. In some cases, nitric oxide may be preferentially toxic to sebum production sites over keratinocytes sites such that sebum production site size or quantity may be reduced without a substantial reduction in keratinocyte viability, or other viable cells in the dermis or epidermis. For example, at some dose levels, the toxicity of the nitric oxide may be preferentially toxic to sebum production sites over keratinization sites by a ratio of 2:1, 3:1 or even 4:1.

Separately, nitric oxide may also modulate the regulatory mechanism for sebum production. The levels of nitric oxide required to modulate lipogenesis may be less than those that are toxic to sebum production sites. Additionally, at some levels, sebum production may be affected by both modulation of lipogenesis and a reduction in size or number of the sebum production sites. Accordingly, some embodiments of the present invention may provide levels of nitric oxide that are non-toxic to sebocytes but that are effective at down regulating lipogenesis, that are toxic to the sebum production sites, or both.

Gaseous Nitric Oxide

In some embodiments, methods of decreasing sebum production include applying gaseous nitric oxide directly or indirectly to the skin of a subject. Applying nitric oxide "directly" refers to applying gaseous nitric oxide to the surface of the skin, without any barriers between the gas flow and the skin. Applying the gaseous nitric oxide "indirectly" refers to application of gaseous nitric oxide through a substrate, such as a cloth, dressing, membrane, medicament, powder, ointment and the like, prior to reaching the skin.

Gaseous nitric oxide may be applied to the skin at any suitable pressure, flow rate, and/or concentration, and may be applied for any suitable length of time. It may be applied in a sealed system (e.g., a mask or chamber affixed over the affected area) or it may be freely flowed over the surface of the skin. The gaseous nitric oxide may also be present in a mixture of gases, or may be applied by itself. Furthermore, gaseous nitric oxide may be used in combination (before, concurrently and/or after) with any other treatment, including any other method described herein and any known anti-acne regimen or treatment.

Nitric Oxide Source

In some embodiments of the invention, methods of decreasing sebum production include applying at least one nitric oxide source directly or indirectly to the skin. Applying a nitric oxide source "directly" refers to applying a nitric oxide source directly on the surface of the skin, without any barriers between the nitric oxide source and the skin. Applying the gaseous nitric oxide "indirectly" refers to application of a nitric oxide source through a substrate, such as a cloth, dressing, membrane, or on top of another medicament, powder, ointment and the like. The term "nitric oxide source" refers to a compound, or other composition or device that provides nitric oxide to the skin, but is not gaseous nitric oxide. In some embodiments, the nitric oxide source includes a nitric oxide-releasing compound, hereinafter referred to as a "NO-releasing compound." An NO-releasing compound includes at least one NO donor, which is a functional group that can release nitric oxide under certain conditions.

Any suitable NO-releasing compound may be used. In some embodiments, the NO-releasing compound includes a small molecule compound that includes an NO donor group. Small molecule compounds are defined herein as compounds having a molecular weight of less than 500 daltons, and include organic and/or inorganic small molecules. In some embodiments, the NO-releasing compound includes a macromolecule that includes an NO donor group. A macromolecule is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from 0.1 nm-100 µm and may comprise the aggregation of two or more macromolecules, whereby the macromolecular structure is further modified with an NO donor group.

In some embodiments of the invention, the NO donor of the NO-releasing compound releases nitric oxide upon exposure to an external condition, such as light, heat, water, acid, base, and the like. For example, in some embodiments, the NO-releasing compound includes a diazeniumdiolate functional group as an NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light. Examples of other NO donor groups include nitrosamine, hydroxyl nitrosamine, hydroxylamine and hydroxyurea. Any suitable combination of NO donors and/or NO-releasing compounds may also be used in the methods described herein. Additionally, the NO donor may be incorporated into or onto the small molecule or macromolecule through covalent and/or non-covalent interactions.

In some embodiments of the invention, the NO-releasing macromolecules may be in the form of NO-releasing particles, such as those described in U.S. Publication No. 2009/0214618, the disclosure of which is incorporated by reference herein in its entirety. Such particles may be prepared by methods described therein.

As an example, in some embodiments of the invention, the NO-releasing particles include NO-loaded precipitated silica. The NO-loaded precipitated silica may be formed from nitric oxide donor modified silane monomers into a co-condensed siloxane network. In one embodiments of the invention, the nitric oxide donor is an N-diazeniumdiolate.

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method can be used to create co-condensed siloxane networks and materials more densely functionalized with NO-donors.

The co-condensed siloxane network can be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula $Si(OR)_4$, wherein R is an alkyl group. The R groups can be the same or different. In some embodiments the tetraalkoxysilane is selected as tetramethyl orthosilicate (TMOS) or tetraethyl orthosilicate (TEOS). In some embodiments, the aminoalkoxysilane has the formula: $R''—(NH—R')_n—Si(OR)_3$, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane can be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl)phenethyltrimethoxysilane (AEMP3); [3-(methylamino)propyl]trimethoxysilane (MAP3); N-butylaminopropyltrimethoxysilane (n-BAP3); t-butylaminopropyltrimethoxysilane (t-BAP3); N-ethylaminoisobutyltrimethoxysilane (EAiB3); N-phenylamino-propyltrimethoxysilane (PAP3); and N-cyclohexylaminopropyltrimethoxysilane (cHAP3).

In some embodiments, the aminoalkoxysilane has the formula: $NH[R'—Si(OR)_3]_2$, wherein R is alkyl and R' is alkylene. In some embodiments, the aminoalkoxysilane can be selected from bis(3-triethoxysilylpropyl)amine, bis-[3-(trimethoxysilyl)propyl]amine and bis-[(3-trimethoxysilyl)propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: $R''—N(NONO^-X^+)—R'—Si(OR)_3$, wherein R is alkyl, R' is alkylene or aralkylene, R" is alkyl or alkylamine, and $X^+$ is a cation selected from the group consisting of $Na^+$, $K^+$ and $Li^+$.

The composition of the siloxane network, (e.g., amount or the chemical composition of the aminoalkoxysilane) and the nitric oxide charging conditions (e.g., the solvent and base) can be varied to optimize the amount and duration of nitric oxide release. Thus, in some embodiments, the composition of the silica particles can be modified to regulate the half-life of NO release from silica particles.

In another embodiment, the amino group of aminoalkoxysilane is substituted with a diazeniumdiolate, and the aminoalkoxysilane having a formula of $R''—N(NONO^-X^+)—R'—Si(OR)_3$, wherein: R is alkyl, R' is alkylene or aralkylene, R" is alkyl or alkylamine, and $X^+$ is a cation selected from the group consisting of $Na^+$ and K.

In some embodiments of the invention, the particle size of the NO-releasing particles is in a range of 20 nm and 10 µM. The particle size may be tailored to minimize or prevent toxicity and penetration through the epidermis (or compromised dermis) and into the blood vessels.

In another embodiment, the NO-releasing composition is S-nitrogluthione (GNSO)

Pharmaceutically Acceptable Compositions

In some embodiments, at least one NO-releasing compound is applied to the skin in a pharmaceutically acceptable composition. As such, at least one nitric oxide source is present in the pharmaceutically acceptable compositions. A pharmaceutically acceptable composition, as defined herein, refers to a composition that is suitable for application to a subject, such as a human, without undue side effects such as toxicity or irritation to the skin. Undue side effects are those that render the composition unsuitable for application to a subject because the harm from the side effects outweighs the benefits of the composition. In some embodiments, pharmaceutically acceptable compositions include at least one NO-releasing compound; optionally, at least one additional therapeutic agent; and at least one pharmaceutically acceptable excipient.

The NO-releasing compounds may be present in pharmaceutically acceptable compositions according to embodiments of the invention at any suitable concentration, but in some embodiments, the NO-releasing compounds are present in the compositions at a concentration sufficient to decrease, eliminate or prevent acne and/or decrease sebum production. In some embodiments, the concentration of NO-releasing compounds ranges from 0.1% to 20% w/w in the composition.

As described above, in some embodiments, pharmaceutically acceptable compositions include at least one additional therapeutic agent, such as those that have antimicrobial, anti-inflammatory, pain-relieving, immunosuppressant, or vasodilating properties. Other anti-acne therapeutic agents such as retinoids may also be included in compositions according to an embodiment of the invention.

The pharmaceutically acceptable compositions may be present in any physical form, such as ointments, creams, milks, pomades, powders, impregnated pads, solutions, gels, sprays, lotions or suspensions. They may also be in the form of suspensions of microspheres or nanospheres or of lipid or polymeric vesicles, or of polymeric patches and hydrogels for controlled release. These compositions for topical application may be in anhydrous form, in aqueous form or in the form of an emulsion (e.g., oil in water or water in oil emulsions).

The term excipient refers to "inert" constituents of pharmaceutically acceptable compositions. The term "inert" indicates that such constituents are not therapeutic agents such as NO-releasing compounds or other antimicrobial compounds, anti-inflammatory agents, pain-relievers, immunosuppressants and vasodilators. However, as one of ordinary skill in the art will understand, the excipients may provide beneficial or therapeutic action to the skin (e.g., moisturize) that may directly affect the acne. The excipients may also indirectly affect the treatment of acne by affecting the activity of the NO-releasing compounds or other therapeutic agents within the compositions.

Excipients for use in topical formulations are well-known in the art and examples may be found in the *Handbook of Pharmaceutical Excipients* (Rowe, R. C. et al., APhA Publications; 5$^{th}$ ed., 2005). Exemplary excipients may include talc, calcium carbonate, calcium phosphate, magnesium stearate, waxes, various sugars and types of starch, polymers, gels, emollients, thickening agents, rheology modifiers, humectants, glycerol, organic basic compounds, cellulose derivatives, gelatin, vegetable oils, polyethylene glycols and solvents. Examples of rheology modifiers include Carbopol, $C_{26-28}$ alkyl dimethicone, $C_{26-28}$ alkyl methicone, polyphenylsisquioxane, trimethylsiloxysilicate, crosspolymers of cyclopentasiloxane and dimethicone/vinyltrimethylsiloxysilicate, and mixtures thereof. Examples of emollients include glycerine, pentylene glycol, sodium pyrrolidone carboxylic acid, lanolin, saccharide isomerate, stearoxy dimethicone, stearyl dimethicone, and mixtures thereof. Emollients may be useful to prevent stratum corneum dehydration occurring due to the use of anhydrous solvents in the formulation. Examples of organic bases include methanolamines, triethanolamines, Trisamino, AMP-95, AmP-Ultra PC 2000, triisopropanolamine, diisopropanolamine, Neutrol TE, Ethomeen, and mixtures thereof. The organic base may render the pH of the medicament basic or neutral, and may directly affect the release of NO from the NO-releasing compounds that include diazeniumdiolate NO donor groups by slowing donor decomposition with increasing alkalinity.

Other exemplary excipients include water-soluble porogens. A water-soluble porogen is an additive that may facilitate water uptake and diffusion into the pharmaceutically acceptable composition. Any suitable porogen may be used, but in some embodiments, the porogen may include sodium chloride, sucrose, glucose, lactose, sorbitol, xylitol, polyethylene glycol, polyvinylpyrrollidone, polyvinyl alcohol or mixtures thereof. Electrolytes, such as NaCl, may also be added as excipients.

Polymers may also act as excipients. Exemplary polymers include hydrophilic polyurethanes, hydrophilic polyacrylates, co-polymers of carboxymethylcellulose and acrylic acid, N-vinylpyrrolidone, poly(hydroxy acids), polyanhydrides, polyorthoesters, polyamides, polycarbonates, polyalkylenes (e.g., polyethylene and polypropylene), polyalkylene glycols (e.g., poly(ethylene glycol)), polyalkylene oxides (e.g., polyethylene oxide), polyalkylene terephthalates (e.g., polyethylene terephthalate), polyvinyl alcohols, polyvinyl ethers, polylvinyl esters, polyvinyl halides (e.g., poly(vinyl chloride)), polyvinylpyrrolidone, polysiloxanes; poly(vinyl acetates), polystyrenes, polyurethane copolymers, cellulose, derivatized celluloses, alginates, poly(acrylic acid), poly(acrylic acid) derivatives, acrylic acid copolymers, methacrylic acid, methacrylic acid derivatives, methacrylic acid copolymers, poly(butyric acid), poly(valeric acid), poly (lactide-co-caprolactone), copolymers thereof and blends thereof.

In some embodiments of the invention, the polymers may be superabsorbent polymers (SAPs). A polymer is considered superabsorbent, as defined per IUPAC, as a polymer that can absorb and retain extremely large amounts of water relative to its own mass. SAPs may absorb water up to 500 times their own weight and may swell up to 1000-times their original volume. Particular SAPs of interest include sodium polyacrylate, the polyurethane Tecophilic TG-2000, and polymers prepared by the use of polyacrylamide copolymer, ethylene maleic anhydride copolymer, cross-linked carboxy-methylcellulose, polyvinyl alcohol copolymers, polyvinylpyrrolindone and cross-linked polyethylene oxide. In some embodiments, the SAP may absorb water from the skin, thereby causing NO to release from the NO-releasing compounds.

In some embodiments of the invention, polymers that are relatively hydrophobic may be used. Any suitable hydrophobic polymer may be used. However, exemplary polymers that are relatively hydrophobic include aromatic polyurethanes, silicone rubber, polysiloxanes, polycaprolactone, polycarbonate, polyvinylchloride, polyethylene, poly-L-lactide, poly-DL-glycolide, polyetheretherketone (PEEK), polyamide, polyimide and polyvinyl acetate. In addition, a hydrophobic gel-base and/or rheology modifier may be used.

In some embodiments of the invention, notably in gels, the polymers may act as thickening agents in the medicaments. Specifically, the polymeric portion of the gel may act as a visco-elastic substance and may retain the gel at the site of application, along with the NO-releasing compounds dispersed therein.

In some other embodiments, notably in gels and ointments, a medicament that includes a polymer may have spreadability such that it forms a thin film when applied on the skin surface. This film may enable the application of the contained NO-releasing compounds over a wide area, and may serve to maintain the NO-releasing compounds on the affected area of the skin.

Other excipients may include various ionic or non-ionic compounds to maintain stability of the formulation, thereby protecting from the de-emulsification, settling, agglomeration or degradation of the formulation constituents that may reduce its therapeutic or aesthetic value.

Examples of ionic compounds may include salts such as sodium chloride, potassium chloride; cationic, anionic or zwitterionic surfactants such as sodium dodecyl sulfate (SDS), perfluorooctanoate (PFOA), perfluorooctanesulfonate (PFOS), ammonium lauryl sulfate (ALS), sodium lauryl ether sulfate (SLES), alkyl benzene sulfonate, cetyl trimethylammonium bromide (CTAB), cetylpyridinium chloride (CPC), polyethoxylated tallow amine (POEA), benzalkonium chloride (BAC), benzethonium chloride, dodecyl betaine, cocamidopropyl betaine and cocoamphoglycinate.

Examples of non-ionic compounds that may act as excipients include non-ionic surfactants such as Pluronic, Tween, AMP, and Brij family of surfactants; and surfactants derived from biological sources, e.g., natural or semi-synthetic surfactants, such as oleic acid, sorbitan trioleate, sorbitan monooleate, lecithin, cocamide MEA, cocamide DEA and cocamidopropyl betaine. Surfactants (both ionic and non-ionic) may reduce the interfacial surface energy and may facilitate spreading of the ointment or liquid over a wider area.

In some embodiments of the invention, solvent excipients may be used as a carrier vehicle for the NO-releasing compounds and other excipients. The polymer chains may interact with the solvent and undergo swelling to form a network that may impart visco-elastic properties to the medicament. In some embodiments of the medicament, the solvent may evaporate upon application, leaving a residual film of the polymer along with the entrapped NO-releasing compounds.

Examples of solvent excipients include dimethyl isosorbide, propylene glycol, glycerol, isopropanol, ethanol, ethylene glycol, polyethylene glycol, ethoxydiglycol or mixtures thereof. Exemplary solvent excipients that may be useful in hydrophobic formulations may include isododecane, isodecyl neopentanoate, butylene glycol, pentylene glycol, hexylene glycol, methoxypolyethyleneglycol, cyclopentasiloxane, cyclotetrasiloxane, dimethicone, caprylyl methicone or mixtures thereof.

In addition to the NO-releasing molecules, excipients, and other therapeutic agents, the pharmaceutically acceptable compositions may also include other compounds that improve the organoleptic properties of the composition. Examples of such compounds include perfumes, dyes and colorants; chelating agents including but not limited to EDTA, EGTA, CP94, citric acid; preservatives including but not limited to quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

Methods of Treatment

As discussed above, provided according to some embodiments of the invention are methods of decreasing sebum production in the skin of a subject by applying gaseous nitric oxide and/or at least one nitric oxide source to the skin. Decrease of acne may be detected by a visual reduction in the amount or severity of the acne and/or by decrease in pain or discomfort associated with the acne, as identified by the subject. The methods of decreasing sebum production in the skin of a subject by applying gaseous nitric oxide and/or at least one nitric oxide source to the skin may be used on those subjects having an overproduction of sebum in the skin. In some cases, decreasing the sebum production in the skin, particularly in those subjects that have an overproduction of sebum, may decrease, eliminate or prevent acne.

In some embodiments, the gaseous nitric oxide, the at least one nitric oxide source and/or a pharmaceutically acceptable composition according to embodiments of the invention are applied topically to the skin of the subject. Any portion of the subject's skin may be treated. However, in some embodiments, the subject's face is treated by a method described herein. Furthermore, in some embodiments, the subject's trunk is treated by a method described herein.

Additionally, in some embodiments, the gaseous nitric oxide, the at least one nitric oxide source and/or a pharmaceutically acceptable composition according to embodiments of the invention are applied in another manner, such as systemic application. As used herein, systemic application refers to application that introduces the nitric oxide, the at least one nitric oxide source and/or the pharmaceutically acceptable composition throughout the body. Furthermore, in some embodiments, the gaseous nitric oxide, the at least one nitric oxide source and/or the pharmaceutically acceptable composition may be applied to the subject parenterally, orally, buccally, subcutaneously, via inhalation, intratracheally, surgically, transdermally, or by any other method known in the art for introduction of a medicament to the body.

Subjects suitable to be treated with a method embodiment of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The invention can also be carried out on animal subjects, particularly mammalian subjects such as mice, rats, dogs, cats, livestock and horses for veterinary purposes, and for drug screening and drug development purposes.

In some embodiments, methods of decreasing sebum production may include using a method described herein in combination with another therapeutic regimen and/or in combination with other medicaments, such as those that have antimicrobial, anti-inflammatory, pain-relieving, immunosuppressant, vasodilating properties, and/or anti-acne properties. For example, other anti-acne agents such as retenoids, may be used in conjunction (prior, concurrently or after) with the application of the gaseous nitric oxide and/or at least one nitric oxide source. As such, in some embodiments of the invention, a patient may be treated with gaseous nitric oxide, at least one NO source and/or a composition described herein in combination with an additional therapeutic agent when the additional therapeutic agent is not in the same composition. For example, in some embodiments, an additional therapeutic agent may be administered (e.g., topically, systemically, parenterally, orally, buccally, subcutaneously, via inhalation, intratracheally, surgically, transdermally, etc.), either concurrently and/or sequentially with application of nitric oxide, at least one nitric oxide source and/or a pharmaceutically acceptable composition that includes at least one nitric oxide source.

In some embodiments of the invention, a pharmaceutically acceptable composition may be administered to the skin via spray delivery. A non-aqueous delivery propellant may be used for water sensitive NO-releasing compounds such as diazeniumdiolate-modified compounds. Further, in some embodiments, particular components of the medicaments may be separated at some point prior to application of the medicament. For example, a water reactive NO-releasing compound may be stored separately from an aqueous component or propellant until application (e.g., via spraying or applying a gel). In some embodiments, the NO-releasing compounds may be combined with an aqueous constituent prior to application or the NO-releasing compounds and an aqueous constituent may be applied to the skin sequentially.

In some embodiments, an ointment containing nitrosothiol-modified compounds may be kept at a low temperature (e.g., <0° C.) to minimize thermal decomposition and NO release. The cold ointment may then be applied to the skin, and the elevated temperature of the skin may allow for the release of NO. In some embodiments, the nitrosothiol may be present in a medicament (e.g., a hydrophilic formulation which may limit NO diffusion) such that it is stable at room temperature due to cage effects, and then releases NO upon application to the skin. Light may also be applied to a medicament that includes nitrosothiol modified compounds. The application of light in fluxes may be applied to create fluxes of NO.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention will be further illustrated by the following non-limiting examples.

EXAMPLES

It is known that increase in dermal lipogenesis is associated with increased sebum production and increased severity of acne. Thus an experiment was designed to determine if applying a nitric oxide source would decrease lipogenesis stimulated by 1 μg/mL insulin in SEB-1 sebocytes.

Example 1

The cytotoxicity of Nitricil™-NJ0109 available from Novan, Inc., Durham, N.C. was determined. Nitricil™-NJ0109 is an NO-releasing co-condensed silica. Cytotoxicity was determined in normal human keratinocytes (NHEK, Lonza) using the Cell Titer-Blue® Cell Viability Assay (Promega). Cells were grown to near confluence in 96-well plates. Prior to treatment, growth media was removed and replaced with serum-free media containing insulin in order to mimic the conditions used in lipogenesis assays. Nitricil™-NJ0109 particles (1, 0.5, 0.1 mg/mL) were added to wells and cell viability was assessed after 24, 48, and 72 hours (n=3 per treatment per time point). Results are shown in Table 1.

TABLE 1

Cytotoxicity of NJ0109 to human sebocytes (SEB-1) and keratinocytes (NHEK). Cytoxicity is expressed in reference to cells incubated with media alone.

| Nitricil | % SEB-1 Killed | | | % NHEK Killed | | |
|---|---|---|---|---|---|---|
| NJ0109 | 24 hr | 48 hr | 72 hr | 24 hr | 48 hr | 72 hr |
| 1 mg/mL | 64% | 78% | 67% | 24% | 29% | 31% |
| 0.5 mg/mL | 40% | 54% | 41% | 26% | 6% | 9% |
| 0.1 mg/mL | 0% | 19% | 15% | −10% | −24% | −4% |

The Nitricil™-NJ0109 particles were more toxic to sebocytes than keratinocytes at all concentrations and time points.

Next, the ability of nontoxic concentrations of Nitricil™-NJ0109 particles to affect lipogenesis in insulin-activated SEB-1 cells was studied. Cells were induced with insulin 1 μg/mL) in order to ensure that lipogenesis levels, which are very low in SEB-1 under standard culture conditions, were boosted sufficiently to detect a treatment-induced decrease. Total lipid production was assayed by measuring the amount of $^{14}C$-acetate incorporation in to neutral lipids. As shown in Table 2, at concentrations that are not cytotoxic to SEB-1 cells, Nitricil™-NJ0109 reduced lipogenesis by up to 17% within 24 hours.

TABLE 2

The effect of NJ0109 on total lipid production in insulin-stimulated SEB-1 sebocytes.

| Treatment | Total Lipid Production[†] | % Reduction | P-value[‡] |
|---|---|---|---|
| Vehicle | 5030 ± 155 | — | — |
| 0.1 mg/ml NJ0109 | 4430 ± 126 | 11.9 | <0.0002 |
| 0.01 mg/ml NJ0109 | 4170 ± 142 | 17.1 | <0.0001 |
| 0.001 mg/ml NJ0109 | 4830 ± 275 | 4.0 | >0.05 |

[†]Each treatment was performed in triplicate. Values represent average counts per minute/10[6] cells/hr ± SEM from three independent experiments.
[‡]Versus treatment with vehicle (two-tailed Students's t-test).

Example 2

Example 1 was duplicated except the NO-releasing composition was S-nitrogluthione (GSNO) and replaced the Nitricil™ particles. GSNO is available from Cayman Chemical, Ann Arbor, Mich. The results are shown in Tables 3 and 4.

TABLE 3

Cytotoxicity of GSNO to human sebocytes (SEB-1) and keratinocytes (NHEK). Cytoxicity is expressed in reference to cells incubated with media alone.

| GSNO | % SEB-1 Killed | | | % NHEK Killed | | |
|---|---|---|---|---|---|---|
| | 24 hr | 48 hr | 72 hr | 24 hr | 48 hr | 72 hr |
| 1.2 mg/ml | 85% | 97% | 98% | 34% | 53% | 44% |
| 0.6 mg/ml | 48% | 68% | 67% | 8% | −11% | −3% |
| 0.12 mg/ml | 6% | 11% | 19% | 4% | 5% | 15% |

TABLE 4

The effect of GSNO on total lipid production in insulin-stimulated SEB-1 sebocytes.

| Treatment | Total Lipid Production† | % Reduction | P-value‡ |
|---|---|---|---|
| Vehicle | 4430 ± 931 | — | — |
| 0.12 mg/ml GSNO | 4100 ± 740 | 7.4 | >0.05 |
| 0.012 mg/ml GSNO | 3430 ± 459 | 22.6 | <0.001 |
| 0.0012 mg/ml GSNO | 3630 ± 448 | 18.1 | 0.003 |

†Each treatment was performed in triplicate. Values represent average counts per minute/$10^6$ cells/hr ± SEM from three independent experiments.
‡Versus treatment with vehicle (two-tailed Student's t-test).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which we claim is:

1. A method of decreasing sebum production in skin of a subject comprising applying a pharmaceutically acceptable composition comprising a nitric oxide (NO)-releasing compound to the skin of the subject, wherein the NO-releasing compound is present in an amount sufficient to decrease sebum production and is present in the pharmaceutically acceptable composition in an amount of 0.1% to 20% w/w in the composition, wherein the NO-releasing compound consists of N-diazeniumdiolate-functionalized macromolecules.

2. The method of claim 1, wherein the N-diazeniumdiolate-functionalized macromolecules comprise N-diazeniumdiolate co-condensed polysiloxane macromolecules.

3. The method of claim 1, wherein the pharmaceutically acceptable composition comprises at least one other therapeutic agent.

4. The method of claim 1, wherein the nitric oxide is applied at a concentration that is toxic to sebum production sites.

5. The method of claim 1, wherein the nitric oxide is applied at a concentration that is not toxic to sebum production sites.

6. The method of claim 1, wherein the nitric oxide is applied at a concentration that is preferentially toxic to sebum production sites over keratinocytes.

7. A method of decreasing sebum production in skin of a subject comprising applying to the subject a pharmaceutically acceptable composition comprising a therapeutic agent, said therapeutic agent consisting essentially of a nitric oxide (NO)-releasing compound, wherein said NO-releasing compound is present in said composition in an amount sufficient to decrease sebum production in the skin of the subject, wherein the NO-releasing compound consists of N-diazeniumdiolate-functionalized macromolecules.

* * * * *

UNITED STATES PATENT AND TRADEMARK OFFICE
CERTIFICATE OF CORRECTION

PATENT NO. : 8,591,876 B2  
APPLICATION NO. : 13/325826  
DATED : November 26, 2013  
INVENTOR(S) : Bauman et al.

Page 1 of 1

It is certified that error appears in the above-identified patent and that said Letters Patent is hereby corrected as shown below:

In the Specification:
Column 8, Line 60: Please correct "of $Na^+$ and K."
to read -- of $Na^+$ and $K^+$. --

Signed and Sealed this
Seventeenth Day of June, 2014

Michelle K. Lee
*Deputy Director of the United States Patent and Trademark Office*